United States Patent
Lipshutz et al.

[11] Patent Number: 5,856,174
[45] Date of Patent: Jan. 5, 1999

[54] INTEGRATED NUCLEIC ACID DIAGNOSTIC DEVICE

[75] Inventors: Robert J. Lipshutz, Palo Alto; Richard P. Rava, San Jose; Rolfe C. Anderson, Mountain View; Stephen P. A. Fodor, Palo Alto, all of Calif.

[73] Assignee: Affymetrix, Inc., Santa Clara, Calif.

[21] Appl. No.: 589,027

[22] Filed: Jan. 19, 1996

Related U.S. Application Data

[60] Provisional application No. 60/000,859 Jul. 3, 1995 and provisional application No. 60/000,703 Jun. 29, 1995.

[51] Int. Cl.$^6$ .................................................. C12M 1/34
[52] U.S. Cl. ........................... 435/286.5; 435/287.2; 435/288.5; 422/68.1; 422/81
[58] Field of Search ......................... 435/286.1, 286.5, 435/286.7, 287.2, 288.6, 288.7, 6, 91.1, 91.2; 422/68.1, 100, 101, 102, 81; 137/803, 806, 874, 206, 208, 571, 597; 417/118, 121

[56] References Cited

U.S. PATENT DOCUMENTS

| | | |
|---|---|---|
| 4,426,451 | 1/1984 | Columbus ............................ 422/102 |
| 4,676,274 | 6/1987 | Brown ................................... 137/806 |
| 5,126,022 | 6/1992 | Soane et al. . |
| 5,143,854 | 9/1992 | Pirrung et al. . |
| 5,171,132 | 12/1992 | Miyazaki et al. . |
| 5,188,963 | 2/1993 | Stapleton . |
| 5,230,866 | 7/1993 | Shartle et al. ........................ 422/68.1 |
| 5,252,294 | 10/1993 | Kroy et al. . |
| 5,271,724 | 12/1993 | van Lintel . |
| 5,277,556 | 1/1994 | van Lintel . |
| 5,281,516 | 1/1994 | Stapleton et al. . |
| 5,296,375 | 3/1994 | Kricka et al. . |
| 5,304,487 | 4/1994 | Wilding et al. . |
| 5,346,672 | 9/1994 | Stapleton et al. . |
| 5,375,979 | 12/1994 | Trah . |
| 5,382,511 | 1/1995 | Stapleton . |
| 5,384,261 | 1/1995 | Winkler et al. . |
| 5,424,186 | 6/1995 | Fodor et al. . |
| 5,436,129 | 7/1995 | Stapleton . |
| 5,451,500 | 9/1995 | Stapleton . |
| 5,486,335 | 1/1996 | Wilding et al. . |
| 5,498,392 | 3/1996 | Wilding et al. . |
| 5,587,128 | 12/1996 | Wilding et al. ..................... 435/287.2 |
| 5,589,350 | 12/1996 | Bochner ............................... 435/288.5 |
| 5,660,993 | 8/1997 | Cathey et al. ...................... 435/287.2 |

FOREIGN PATENT DOCUMENTS

| | | | |
|---|---|---|---|
| WO 90/15070 | 12/1990 | WIPO | ............................ C07K 1/04 |
| WO 92/10092 | 6/1992 | WIPO | ............................ A01N 1/02 |
| WO 93/09668 | 5/1993 | WIPO | ............................ A01N 1/02 |
| WO 94/05414 | 3/1994 | WIPO | ............................ B01F 11/02 |

OTHER PUBLICATIONS

Stix. "Gene Readers." Scientific American. Jan. 1994, pp. 149–150.

(List continued on next page.)

*Primary Examiner*—William H. Beisner
*Attorney, Agent, or Firm*—Townsend and Townsend and Crew LLP

[57] ABSTRACT

The present invention provides a miniaturized integrated nucleic acid diagnostic device and system. The device of the invention is generally capable of performing one or more sample acquisition and preparation operations, in combination with one or more sample analysis operations. For example, the device can integrate several or all of the operations involved in sample acquisition and storage, sample preparation and sample analysis, within a single integrated unit. The device is useful in a variety of applications, and most notably, nucleic acid based diagnostic applications and de novo sequencing applications.

4 Claims, 17 Drawing Sheets

OTHER PUBLICATIONS

Bart et al., "Microfabricated Electrohydrodynamic Pumps," *Sensors and Actuators*, A21–A23:193–197 (1990).

Effenhauser et al., "Glass Chips for High–Speed Capillary Electrophoresis Separations with Submicrometer Plate Heights," *Anal. Chem.*, 65:2637–2642 (1993).

Effenhauser et al., "High–Speed Separation of Antisense Oligonucleotides on a Micromachined Capillary Electrophoresis Device," *Anal. Chem.*, 66:2949–2953 (1994).

Fodor et al., "Light–Directed, Spatially Addressable Parallel Chemical Synthesis," *Science*, 251:767–777 (1991).

Ghandi, *VLSI Fabrication Principles*, 2nd ed., John Wiley & Sons, Inc., Ch. 10, (1994).

Harrison et al., "Micromachining a Miniaturized Capillary Electrophoresis–Based Chemical Analysis System on a Chip," *Science*, 261:895–897 (1993).

Horowitz and Hill, *The Art of Electronics*, 2d. ed., Cambridge University Press, Ch. 15, (1994).

Jacobsen et al., "High–Speed Separationson a Microchip," *Anal. Chem.*, 66:1114–1118 (1994).

Luckey et al., "A model for the mobility of single–stranded DNA in capillary gel electrophoresis," *Electrophoresis*, 14:492–501 (1993).

Manz et al., "Planar chips technology for miniaturization and integration of separation techniques into monitoring systems: Capillary electrophoresis on a chip," *J. Chromatog.*, 593:253–258 (1992).

Pease et al., "Light–generated oligonucleotide arrays for rapid DNA sequence analysis," *PNAS*, 91:5022–5026 (1994).

Richter et al., "An Electrohydrodynamic Micropump," 3rd IEEE Workshop on Micro Electro Mechanical Systems, Feb. 12–14, 1990, Napa Valley.

Richter et al., "A micromachined electrohydrodynamic (EHD) pump," *Sensors and Actuators*, 29:159–165 (1991).

Woolley and Mathies, "Ultra high–speed DNA fragment separations using microfabricated capillary array electrophoresis chips," *PNAS*, 91:11348–11352 (1994).

*Physical Acoustics, Principles and Methods*, vol. 2, Part B, Mason, ed., Academic Press, (1965).

*Piezoelectric Technology, Data for Engineers*, Clevite Corp. No Date Provided.

Flow Visualization

Checkerboard Oligo Test Pattern

Effect of Fragmentation Time at 94C t =   0   5   10   30   60   120 minutes

Correct Call Rates:
        74%       95.8%      95.9%
           95.9%     95.5%      83% ated micro-PCR apparatus for collection and amplification of nucleic acids from a specimen. U.S. Pat. Nos. 5,304,487 to Wilding et al., and 5,296,375 to Kricka et al., discuss devices for collection and analysis of cell containing samples. However, there remains a need for an apparatus which combines the various processing and analytical operations involved in nucleic acid analysis. The present invention meets these and other needs.

INTEGRATED NUCLEIC ACID DIAGNOSTIC DEVICE

The present invention was made with U.S. Government support under ATP Grant No. 70NANB51031, and the government may have certain rights in the invention.

CROSS REFERENCE TO RELATED APPLICATIONS

The present application is a regular application claiming priority from Provisional U.S. patent application Ser. No. 60/000,703, filed Jun. 29, 1995, and Provisional U.S. patent application Ser. No. 60/000,859, filed Jul. 3, 1995, and incorporated herein by reference in its entirety for all purposes.

BACKGROUND OF THE INVENTION

The relationship between structure and function of macromolecules is of fundamental importance in the understanding of biological systems. These relationships are important to understanding, for example, the functions of enzymes, structure of signalling proteins, ways in which cells communicate with each other, as well as mechanisms of cellular control and metabolic feedback.

Genetic information is critical in continuation of life processes. Life is substantially informationally based and its genetic content controls the growth and reproduction of the organism. The amino acid sequences of polypeptides, which are critical features of all living systems, are encoded by the genetic material of the cell. Further, the properties of these polypeptides, e.g., as enzymes, functional proteins, and structural proteins, are determined by the sequence of amino acids which make them up. As structure and function are integrally related, many biological functions may be explained by elucidating the underlying structural features which provide those functions, and these structures are determined by the underlying genetic information in the form of polynucleotide sequences. In addition to encoding polypeptides, polynucleotide sequences can also be specifically involved in, for example, the control and regulation of gene expression.

The study of this genetic information has proved to be of great value in providing a better understanding of life processes, as well as diagnosing and treating a large number of disorders. In particular, disorders which are caused by mutations, deletions or repeats in specific portions of the genome, may be readily diagnosed and/or treated using genetic techniques. Similarly, disorders caused by external agents may be diagnosed by detecting the presence of genetic material which is unique to the external agent, e.g., bacterial or viral DNA.

While current genetic methods are generally capable of identifying these genetic sequences, such methods generally rely on a multiplicity of distinct processes to elucidate the nucleic acid sequences, with each process introducing a potential for error into the overall process. These processes also draw from a large number of distinct disciplines, including chemistry, molecular biology, medicine and others. It would therefore be desirable to integrate the various process used in genetic diagnosis, in a single process, at a minimum cost, and with a maximum ease of operation.

Interest has been growing in the fabrication of microfluidic devices. Typically, advances in the semiconductor manufacturing arts have been translated to the fabrication of micromechanical structures, e.g., micropumps, microvalves and the like, and microfluidic devices including miniature chambers and flow passages.

A number of researchers have attempted employ these microfabrication techniques in the miniaturization of some of the processes involved in genetic analysis in particular. For example, published PCT Application No. WO 94/05414, to Northrup and White, incorporated herein by reference in its entirety for all purposes, reports an integrated micro-PCR apparatus for collection and amplification of nucleic acids from a specimen. U.S. Pat. Nos. 5,304,487 to Wilding et al., and 5,296,375 to Kricka et al., discuss devices for collection and analysis of cell containing samples. However, there remains a need for an apparatus which combines the various processing and analytical operations involved in nucleic acid analysis. The present invention meets these and other needs.

SUMMARY OF THE INVENTION

The present invention generally provides miniature analytical devices that include a plurality of distinct reaction chambers disposed in a single, miniature body. Each of the reaction chambers is fluidly connected to at least one other of said reaction chambers. The device includes a sample inlet, fluidly connected to at least one of said plurality of reaction chambers, for introducing a fluid sample into said device, a fluid transport system for moving a fluid sample from at least a first reaction chamber of said plurality of reaction chambers to at least a second reaction chamber of said plurality of reaction chambers and a hybridization chamber for analyzing a component of said fluid sample, said hybridization chamber being fluidly connected to at least one of said plurality of reaction chambers and including a polymer array, said polymer array including a plurality of different polymer sequences coupled to a surface of a single substrate, each of said plurality of different polymer sequences being coupled to said surface in a different, known location.

In another embodiment, the miniature devices of the invention include one or more microcapillary channels for analyzing a component of a fluid sample. The microcapillary channels are typically fluidly connected to at least one of the reaction chambers in the body of the device and include at least first and second electrodes at opposite ends of the microcapillary channel for applying a voltage across the microcapillary channel.

In a further aspect, the devices of the invention incorporate an in vitro transcription reaction chamber having an effective amount of an RNA polymerase and four different nucleoside triphosphates, disposed therein.

In a related embodiment, the present invention also provides devices which include an amplification reaction chamber, the amplification reaction chamber having one or more amplification reagents disposed therein, in combination with a reaction chamber incorporating an oligonucleotide array.

In still another aspect, the devices of the invention may include a temperature controlled reaction chamber, and/or a mixing sytem for mixing the contents of a reaction chamber included in the device.

In an additional aspect, the devices of the invention may include a central pumping chamber disposed within the body. The central pumping chamber is fluidly connected to each of the plurality of reaction chambers by one of a plurality of fluid passages. Each of the plurality of fluid passages includes a valve disposed across the fluid passage, whereby the fluid passages may be selectively opened and closed to direct a fluid sample from a first reaction chamber through the central pumping chamber and into a second reaction chamber.

In another aspect, the devices of the present invention incorporate a fluid transport system that includes a differential pressure delivery system for maintaining a first reaction chamber at a first pressure and a second reaction chamber at a second pressure. The first pressure is greater than ambient pressure and the second pressure is greater than the first pressure, whereby when the second reaction chamber is brought to ambient pressure, the first pressure forces a liquid sample in the first reaction chamber into the second reaction chamber.

In a related aspect, the fluid transport system includes a differential pressure delivery source for maintaining the first reaction chamber at a first pressure and said second reaction chamber at a second pressure. In this aspect, however, the second pressure is less than ambient pressure and the first pressure is less than the second pressure, whereby when the first reaction chamber is brought to ambient pressure, the second pressure draws a liquid sample in the first reaction chamber into the second reaction chamber.

BRIEF DESCRIPTION OF THE DRAWINGS

FIGS. 4A and 4B show the microcapillary configured for carrying out alternate loading strategies for the microcapillary whereas FIG. 4C illustrates the microcapillary in running mode.

FIG. 6 shows schematic illustrations of pneumatic control manifolds for transporting fluid within a miniature integrated device. FIG. 6A shows a manifold configuration suitable for application of negative pressure, or vacuum, whereas

DETAILED DESCRIPTION OF THE INVENTION

I. General

Figure 1:
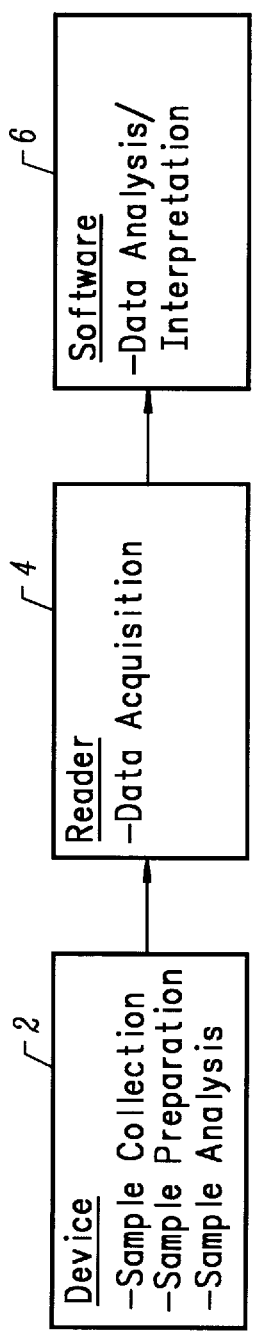
FIG. 1 shows a schematic representation of a nucleic acid diagnostic system for analysis of nucleic acids from samples.

It is a general object of the present invention to provide a miniaturized integrated nucleic acid diagnostic device and system. The device of the invention is generally capable of performing one or more sample acquisition and preparation operations, in combination with one or more sample analysis operations. For example, the device can integrate several or all of the operations involved in sample acquisition and storage, sample preparation and sample analysis, within a single, miniaturized, integrated unit. The device is useful in a variety of applications and most notably, nucleic acid based diagnostic applications and de novo sequencing applications.

The device of the invention will typically be one component of a larger diagnostic system which further includes a reader device for scanning and obtaining the data from the device, and a computer based interface for controlling the device and/or interpretation of the data derived from the device.

To carry out its primary function, one embodiment of the device of the invention will incorporate a plurality of distinct reaction chambers for carrying out the sample acquisition, preparation and analysis operations. In particular, a sample to be analyzed is introduced into the device whereupon it will be delivered to one of several distinct reaction chambers which are designed for carrying out a variety of reactions as a prelude to analysis of the sample. These preparative reactions generally include, e.g., sample extraction, PCR amplification, nucleic acid fragmentation and labeling, extension reactions, transcription reactions and the like.

Following sample preparation, the sample can be subjected to one or more different analysis operations. A variety of analysis operations may generally be performed, including size based analysis using, e.g., microcapillary electrophoresis, and/or sequence based analysis using, e.g., hybridization to an oligonucleotide array. In addition to the various reaction chambers, the device will generally comprise a series of fluid channels which allow for the transportation of the sample or a portion thereof, among the various reaction chambers. Further chambers and components may also be included to provide reagents, buffers, sample manipulation, e.g., mixing, pumping, fluid direction (i.e., valves) heating and the like.

II. Integratable Operations

A. Sample Acquisition

The sample collection portion of the device of the present invention generally provides for the identification of the sample, while preventing contamination of the sample by external elements, or contamination of the environment by the sample. Generally, this is carried out by introducing a sample for analysis, e.g., preamplified sample, tissue, blood, saliva, etc., directly into a sample collection chamber within the device. Typically, the prevention of cross-contamination of the sample may be accomplished by directly injecting the sample into the sample collection chamber through a sealable opening, e.g., an injection valve, or a septum. Generally, sealable valves are preferred to reduce any potential threat of leakage during or after sample injection. Alternatively, the device may be provided with a hypodermic needle integrated within the device and connected to the sample collection chamber, for direct acquisition of the sample into the sample chamber. This can substantially reduce the opportunity for contamination of the sample.

In addition to the foregoing, the sample collection portion of the device may also include reagents and/or treatments for neutralization of infectious agents, stabilization of the specimen or sample, pH adjustments, and the like. Stabilization and pH adjustment treatments may include, e.g., introduction of heparin to prevent clotting of blood samples, addition of buffering agents, addition of protease or nuclease inhibitors, preservatives and the like. Such reagents may generally be stored within the sample collection chamber of the device or may be stored within a separately accessible chamber, wherein the reagents may be added to or mixed with the sample upon introduction of the sample into the device. These reagents may be incorporated within the device in either liquid or lyophilized form, depending upon the nature and stability of the particular reagent used.

B. Sample Preparation

In between introducing the sample to be analyzed into the device, and analyzing that sample, e.g., on an oligonucleotide array, it will often be desirable to perform one or more sample preparation operations upon the sample. Typically, these sample preparation operations will include such manipulations as extraction of intracellular material, e.g., nucleic acids from whole cell samples, viruses and the like, amplification of nucleic acids, fragmentation, transcription, labeling and/or extension reactions. One or more of these various operations may be readily incorporated into the device of the present invention.

C. DNA Extraction

For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g., denaturation of contaminating (DNA binding) proteins, purification, filtration, desalting, and the like.

Liberation of nucleic acids from the sample cells or viruses, and denaturation of DNA binding proteins may generally be performed by physical or chemical methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within the extraction chamber, a separate accessible chamber or externally introduced.

Alternatively, physical methods may be used to extract the nucleic acids and denature DNA binding proteins. U.S. Pat. No. 5,304,487, incorporated herein by reference in its entirety for all purposes, discusses the use of physical protrusions within microchannels or sharp edged particles within a chamber or channel to pierce cell membranes and extract their contents. More traditional methods of cell extraction may also be used, e.g., employing a channel with restricted cross-sectional dimension which causes cell lysis when the sample is passed through the channel with sufficient flow pressure. Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to effect cell lysis/extraction, including, e.g., subjecting cells to ultrasonic agitation, or forcing cells through microgeometry apertures, thereby subjecting the cells to high shear stress resulting in rupture.

Following extraction, it will often be desirable to separate the nucleic acids from other elements of the crude extract, e.g., denatured proteins, cell membrane particles, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g., by binding the nucleic acids to a solid phase and washing away the contaminating salts or performing gel filtration chromatography on the sample. Suitable solid supports for nucleic acid binding include, e.g., diatomaceous earth, silica, or the like. Suitable gel exclusion media is also well known in the art and is commercially available from, e.g., Pharmacia and Sigma Chemical. This isolation and/or gel filtration/desalting may be carried out in an additional chamber, or alternatively, the particular chromatographic media may be incorporated in a channel or fluid passage leading to a subsequent reaction chamber. Alternatively, the interior surfaces of one or more fluid passages or chambers may themselves be derivatized to provide functional groups appropriate for the desired purification, e.g., charged groups, affinity binding groups and the like.

D. Amplification and In Vitro Transcription

Following sample collection and nucleic acid extraction, the nucleic acid portion of the sample is typically subjected to one or more preparative reactions. These preparative reactions include in vitro transcription, labeling, fragmentation, amplification and other reactions. Nucleic acid amplification increases the number of copies of the target nucleic acid sequence of interest. A variety of amplification methods are suitable for use in the methods and device of the present invention, including for example, the polymerase chain reaction method or (PCR), the ligase chain reaction (LCR), self sustained sequence replication (3SR), and nucleic acid based sequence amplification (NASBA).

The latter two amplification methods involve isothermal reactions based on isothermal transcription, which produce both single stranded RNA (ssRNA) and double stranded DNA (dsDNA) as the amplification products in a ratio of approximately 30 or 100 to 1, respectively. As a result, where these latter methods are employed, sequence analysis may be carried out using either type of substrate, i.e., complementary to either DNA or RNA.

In particularly preferred aspects, the amplification step is carried out using PCR techniques that are well known in the art. See *PCR Protocols: A Guide to Methods and Applications* (Innis, M., Gelfand, D., Sninsky, J. and White, T., eds.) Academic Press (1990), incorporated herein by reference in its entirety for all purposes. PCR amplification generally involves the use of one strand of the target nucleic acid sequence as a template for producing a large number of complements to that sequence. Generally, two primer sequences complementary to different ends of a segment of the complementary strands of the target sequence hybridize with their respective strands of the target sequence, and in the presence of polymerase enzymes and nucleoside triphosphates, the primers are extended along the target sequence. The extensions are melted from the target sequence and the process is repeated, this time with the additional copies of the target sequence synthesized in the preceding steps. PCR amplification typically involves repeated cycles of denaturation, hybridization and extension reactions to produce sufficient amounts of the target nucleic acid. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In PCR methods, strand separation is normally achieved by heating the reaction to a sufficiently high temperature for a sufficient time to cause the denaturation of the duplex but not to cause an irreversible denaturation of the polymerase enzyme (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology,* 43:63–67; and Radding, 1982, *Ann. Rev. Genetics* 16:405–436, each of which is incorporated herein by reference). Other embodiments may achieve strand separation by application of electric fields across the sample. For example, Published PCT Application Nos. WO 92/04470 and WO 95/25177, incorporated herein by reference, describe electrochemical methods of denaturing double stranded DNA by application of an electric field to a sample containing the DNA. Structures for carrying out this electrochemical denaturation include a working electrode, counter electrode and reference electrode arranged in a potentiostat arrangement across a reaction chamber (See, Published PCT Application Nos. WO 92/04470 and WO 95/25177, each of which is incorporated herein by reference for all purposes). Such devices may be readily miniaturized for incorporation into the devices of the present invention utilizing the microfabrication techniques described herein.

Template-dependent extension of primers in PCR is catalyzed by a polymerizing agent in the presence of adequate amounts of four deoxyribonucleotide triphosphates (typically DATP, dGTP, dCTP, dUTP and dTTP) in a reaction medium which comprises the appropriate salts, metal cations, and pH buffering system. Reaction components and conditions are well known in the art (See PCR Protocols: A Guide to Methods and Applications (Innis, M., Gelfand, D., Sninsky, J. and White, T., eds.) Academic Press (1990), previously incorporated by reference). Suitable polymerizing agents are enzymes known to catalyze template-dependent DNA synthesis.

Published PCT Application No. WO 94/05414, to Northrup and White, discusses the use of a microPCR chamber which incorporates microheaters and micropumps in the thermal cycling and mixing during the PCR reactions.

The amplification reaction chamber of the device may comprise a sealable opening for the addition of the various amplification reagents. However, in preferred aspects, the amplification chamber will have an effective amount of the various amplification reagents described above, predisposed within the amplification chamber, or within an associated reagent chamber whereby the reagents can be readily transported to the amplification chamber upon initiation of the amplification operation. By "effective amount" is meant a quantity and/or concentration of reagents required to carry out amplification of a targeted nucleic acid sequence. These amounts are readily determined from known PCR protocols. See, e.g., Sambrook, et al. *Molecular Cloning: A Laboratory Manual,* (2nd ed.) Vols. 1–3, Cold Spring Harbor Laboratory, (1989) and *PCR Protocols: A Guide to Methods and Applications* (Innis, M., Gelfand, D., Sninsky, J. and White, T., eds.) Academic Press (1990), both of which are incorporated herein by reference for all purposes in their entirety. For those embodiments where the various reagents are predisposed within the amplification or adjacent chamber, it will often be desirable for these reagents to be in lyophilized forms, to provide maximum shelf life of the overall device. Introduction of the liquid sample to the chamber then reconstitutes the reagents in active form, and the particular reactions may be carried out.

In some aspects, the polymerase enzyme may be present within the amplification chamber, coupled to a suitable solid support, or to the walls and surfaces of the amplification chamber. Suitable solid supports include those that are well known in the art, e.g., agarose, cellulose, silica, divinylbenzene, polystyrene, etc. Coupling of enzymes to solid supports has been reported to impart stability to the enzyme in question, which allows for storage of days, weeks or even months without a substantial loss in enzyme activity, and without the necessity of lyophilizing the enzyme. The 94 kd, single subunit DNA polymerase from Thermus aquaticus (or tag polymerase) is particularly suited for the PCR based amplification methods used in the present invention, and is generally commercially available from, e.g., Promega, Inc., Madison, Wis. In particular, monoclonal antibodies are available which bind the enzyme without affecting its polymerase activity. Consequently, covalent attachment of the active polymerase enzyme to a solid support, or the walls of the amplification chamber can be carried out by using the antibody as a linker between the enzyme and the support.

E. Labeling and Fragmentation

The nucleic acids in a sample will generally be labeled to facilitate detection in subsequent steps. Labeling may be carried out during the amplification or in vitro transcription processes. In particular, amplification or in vitro transcription may incorporate a label into the amplified or transcribed sequence, either through the use of labeled primers or the incorporation of labeled dNTPs into the amplified sequence.

Alternatively, the nucleic acids in the sample may be labeled following amplification. Post amplification labeling typically involves the covalent attachment of a particular detectable group upon the amplified sequences. Suitable labels or detectable groups include a variety of fluorescent or radioactive labeling groups well known in the art. These labels may also be coupled to the sequences using methods that are well known in the art. See, e.g., Sambrook, et al.

In addition, amplified sequences may be subjected to other post amplification treatments. For example, in some cases, it may be desirable to fragment the sequence prior to hybridization with an oligonucleotide array, in order to provide segments which are more readily accessible to the probes, which avoid looping and/or hybridization to multiple probes. Fragmentation of the nucleic acids may generally be carried out by physical, chemical or enzymatic methods that are known in the art. These additional treatments may be performed within the amplification chamber, or alternatively, may be carried out in a separate chamber. For example, physical fragmentation methods may involve moving the sample containing the nucleic acid over pits or spikes in the surface of a reaction chamber or fluid channel. The motion of the fluid sample, in combination with the surface irregularities produces a high shear rate, resulting in fragmentation of the nucleic acids. In one aspect, this may be accomplished in a miniature device by bonding a piezoelectric element, e.g., a PZT ceramic element to a glass layer that covers a reaction chamber or flow channel. The glass layer has pits or spikes manufactured in the surface which are within the chamber or flow channel. By driving the crystal in the thickness mode, a standing wave is set up within the chamber. Cavitation and/or streaming within the chamber results in substantial shear. Similar shear rates may be achieved by forcing the nucleic acid containing fluid sample through restricted size flow passages, e.g., apertures having a cross-sectional dimension in the micron or submicron scale, thereby producing a high shear rate and fragmenting the nucleic acid.

F. Sample Analysis

Following the various sample preparation operations, the sample will generally be subjected to one or more analysis operations. Particularly preferred analysis operations include, e.g., sequence based analyses using an oligonucleotide array and/or size based analyses using, e.g., microcapillary array electrophoresis.

1. Oligonucleotide Probe Array

In one aspect, following sample preparation, the nucleic acid sample is probed using an array of oligonucleotide probes. Oligonucleotide arrays generally include a substrate having a large number of positionally distinct oligonucleotide probes attached to the substrate. These oligonucleotide arrays, also described as "Genechips™," have been generally described in the art, for example, U.S. Pat. No. 5,143,854 and PCT patent publication Nos. WO 90/15070 and 92/10092. These pioneering arrays may be produced using mechanical or light directed synthesis methods which incorporate a combination of photolithographic methods and solid phase oligonucleotide synthesis methods. See Fodor et al., Science, 251:767–777 (1991), Pirrung et al., U.S. Pat. No. 5,143,854 (see also PCT Application No. WO 90/15070) and Fodor et al., PCT Publication No. WO 92/10092, all incorporated herein by reference. These references disclose methods of forming vast arrays of peptides, oligonucleotides and other polymer sequences using, for example, light-directed synthesis techniques. Techniques for the synthesis of these arrays using mechanical synthesis strategies are described in, e.g., PCT Publication No. 93/09668 and U.S. Pat. No. 5,384,261, each of which is incorporated herein by reference in its entirety for all purposes.

The basic strategy for light directed synthesis of oligonucleotide arrays is as follows. The surface of a solid support, modified with photosensitive protecting groups is illuminated through a photolithographic mask, yielding reactive hydroxyl groups in the illuminated regions. A selected nucleotide, typically in the form of a 3'-O-phosphoramidite-activated deoxynucleoside (protected at the 5' hydroxyl with a photosensitive protecting group), is then presented to the surface and coupling occurs at the sites that were exposed to light. Following capping and oxidation, the substrate is rinsed and the surface is illuminated through a second mask, to expose additional hydroxyl groups for coupling. A second selected nucleotide (e.g., 5'-protected, 3'-O-phosphoramidite-activated deoxynucleoside) is presented to the surface. The selective deprotection and coupling cycles are repeated until the desired set of products is obtained. Since photolithography is used, the process can be readily miniaturized to generate high density arrays of oligonucleotide probes. Furthermore, the sequence of the oligonucleotides at each site is known. See, Pease, et al. Mechanical synthesis methods are similar to the light directed methods except involving mechanical direction of fluids for deprotection and addition in the synthesis steps.

Typically, the arrays used in the present invention will have a site density of greater than 100 different probes per $cm^2$. Preferably, the arrays will have a site density of greater than $500/cm^2$, more preferably greater than about $1000/cm^2$, and most preferably, greater than about $10,000/cm^2$. Preferably, the arrays will have more than 100 different probes on a single substrate, more preferably greater than about 1000 different probes still more preferably, greater than about 10,000 different probes and most preferably, greater than 100,000 different probes on a single substrate.

For some embodiments, oligonucleotide arrays may be prepared having all possible probes of a given length. Such arrays may be used in such areas as sequencing by hybridization ("SBH") applications, which offer substantial benefits over traditional sequencing methods. The use of oligonucleotide arrays in SBH applications is described in, e.g., U.S. patent application Ser. No. 08/505,919, filed Jul. 24, 1995, now abandoned, and U.S. patent application Ser. No. 08/284,064, filed Aug. 2, 1994, now abandoned, each of which is incorporated herein by reference in its entirety for all purposes. These methods typically use a set of short oligonucleotide probes of defined sequence to search for complementary sequences on a longer target strand of DNA. The hybridization pattern of the target sequence on the array is used to reconstruct the target DNA sequence. Hybridization analysis of large numbers of probes can be used to sequence long stretches of DNA.

One strategy of de novo sequencing can be illustrated by the following example. A 12-mer target DNA sequence is probed on an array having a complete set of octanucleotide probes. Five of the 65,536 octamer probes will perfectly hybridize to the target sequence. The identity of the probes at each site is known. Thus, by determining the locations at which the target hybridizes on the array, or the hybridization pattern, one can determine the sequence of the target sequence. While these strategies have been proposed and utilized in some applications, there has been difficulty in demonstrating sequencing of larger nucleic acids using these same strategies. Accordingly, in preferred aspects, SBH methods utilizing the devices described herein use data from mismatched probes, as well as perfectly matching probes, to supply useful sequence data, as described in U.S. patent application Ser. No. 08/505,919, now abandoned, incorporated herein by reference.

While oligonucleotide probes may be prepared having every possible sequence of length n, it will often be desirable in practicing the present invention to provide an oligonucleotide array which is specific and complementary to a particular nucleic acid sequence. For example, in particularly preferred aspects, the oligonucleotide array will contain oligonucleotide probes which are complementary to specific target sequences, and individual or multiple mutations of these. Such arrays are particularly useful in the diagnosis of specific disorders which are characterized by the presence of a particular nucleic acid sequence. For example, the target sequence may be that of a particular exogenous disease causing agent, e.g., human immunodeficiency virus (see, U.S. application Ser. No. 08/284,064, now abandoned, previously incorporated herein by reference), or alternatively, the target sequence may be that portion of the human genome which is known to be mutated in instances of a particular disorder, i.e., sickle cell anemia (see, e.g., U.S. application Ser. No. 08/082,937, now abandoned, previously incorporated herein by reference) or cystic fibrosis.

In such an application, the array generally comprises at least four sets of oligonucleotide probes, usually from about 9 to about 21 nucleotides in length. A first probe set has a probe corresponding to each nucleotide in the target sequence. A probe is related to its corresponding nucleotide by being exactly complementary to a subsequence of the target sequence that includes the corresponding nucleotide. Thus, each probe has a position, designated an interrogation position, that is occupied by a complementary nucleotide to the corresponding nucleotide in the target sequence. The three additional probe sets each have a corresponding probe for each probe in the first probe set, but substituting the interrogation position with the three other nucleotides. Thus, for each nucleotide in the target sequence, there are four corresponding probes, one from each of the probe sets. The three corresponding probes in the three additional probe sets are identical to the corresponding probe from the first probe or a subsequence thereof that includes the interrogation position, except that the interrogation position is occupied by a different nucleotide in each of the four corresponding probes.

Some arrays have fifth, sixth, seventh and eighth probe sets. The probes in each set are selected by analogous principles to those for the probes in the first four probe sets, except that the probes in the fifth, sixth, seventh and eighth sets exhibit complementarity to a second reference sequence. In some arrays, the first set of probes is complementary to the coding strand of the target sequence while the second set is complementary to the noncoding strand. Alternatively, the second reference sequence can be a subsequence of the first reference sequence having a substitution of at least one nucleotide.

In some applications, the target sequence has a substituted nucleotide relative to the probe sequence in at least one undetermined position, and the relative specific binding of the probes indicates the location of the position and the nucleotide occupying the position in the target sequence.

Following amplification and/or labeling, the nucleic acid sample is incubated with the oligonucleotide array in the hybridization chamber. Hybridization between the sample nucleic acid and the oligonucleotide probes upon the array is then detected, using, e.g., epifluorescence confocal microscopy. Typically, the detection operation will be performed using a reader device external to the diagnostic device. However, it may be desirable in some cases, to incorporate the data gathering operation into the diagnostic device itself.

The hybridization data is next analyzed to determine the presence or absence of a particular sequence within the sample, or by analyzing multiple hybridizations to determine the sequence of the target nucleic acid using the SBH techniques already described.

2. Capillary Electrophoresis

In some embodiments, it may be desirable to provide an additional, or alternative means for analyzing the nucleic acids from the sample. In one embodiment, the device of the invention will optionally or additionally comprise a micro capillary array for analysis of the nucleic acids obtained from the sample.

Microcapillary array electrophoresis generally involves the use of a thin capillary or channel which may or may not be filled with a particular separation medium. Electrophoresis of a sample through the capillary provides a size based separation profile for the sample. The use of microcapillary electrophoresis in size separation of nucleic acids has been reported in, e.g., Woolley and Mathies, *Proc. Nat'l Acad. Sci. USA* (1994) 91:11348–11352. Microcapillary array electrophoresis generally provides a rapid method for size based sequencing, PCR product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods.

Microfabrication of microfluidic devices including microcapillary electrophoretic devices has been discussed in detail in, e.g., Jacobsen, et al., *Anal. Chem.* (1994) 66:1114–1118, Effenhauser, et al., *Anal. Chem.* (1994) 66:2949–2953, Harrison, et al., *Science* (1993) 261:895–897, Effenhauser, et al. *Anal. Chem.* (1993) 65:2637–2642, and Manz, et al., *J. Chromatog.* (1992) 593:253–258. Typically, these methods comprise photolithographic etching of micron scale channels on a silica, silicon or other crystalline substrate or chip, and can be readily adapted for use in the miniaturized devices of the present invention. In some embodiments, the capillary arrays may be fabricated from the same polymeric materials described for the fabrication of the body of the device, using the injection molding techniques described herein.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acds in the sample.

In addition to its use in nucleic acid "fingerprinting" and other sized based analyses, the capillary arrays may also be used in sequencing applications. In particular, gel based sequencing techniques may be readily adapted for capillary array electrophoresis. For example, capillary electrophoresis may be combined with the Sanger dideoxy chain termination sequencing methods as discussed in Sambrook, et al. (See also Brenner, et al., *Proc. Nat'l Acad. Sci.* (1989) 86:8902–8906). In these methods, the sample nucleic acid is amplified in the presence of fluorescent dideoxynucleoside triphosphates in an extension reaction. The random incorporation of the dideoxynucleotides terminates transcription of the nucleic acid. This results in a range of transcription products differing from another member by a single base. Comparative size based separation then allows the sequence of the nucleic acid to be determined based upon the last dideoxy nucleotide to be incorporated.

G. Data Gathering and Analysis

Gathering data from the various analysis operations, e.g., oligonucleotide and/or microcapillary arrays, will typically be carried out using methods known in the art. For example, the arrays may be scanned using lasers to excite fluorescently labeled targets that have hybridized to regions of probe arrays, which can then be imaged using charged coupled devices ("CCDs") for a wide field scanning of the array. Alternatively, another particularly useful method for gathering data from the arrays is through the use of laser confocal microscopy which combines the ease and speed of a readily automated process with high resolution detection. Particularly preferred scanning devices are generally described in, e.g., U.S. Pat. Nos. 5,143,854 and 5,424,186.

Following the data gathering operation, the data will typically be reported to a data analysis operation. To facilitate the sample analysis operation, the data obtained by the reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of hybridizing probes, normalization of background and single base mismatch hybridizations, ordering of sequence data in SBH applications, and the like, as described in, e.g., U.S. patent application Ser. No. 08/327,525, filed Oct. 21, 1994, and incorporated herein by reference.

III. The Nucleic Acid Diagnostic System

A. Analytical System

A schematic of a representative analytical system based upon the device of the invention is shown in FIG. 1. The system includes the diagnostic device 2 which performs one or more of the operations of sample collection, preparation and/or analysis using, e.g., hybridization and/or size based separation. The diagnostic device is then placed in a reader device 4 to detect the hybridization and or separation information present on the device. The hybridization and/or separation data is then reported from the reader device to a computer 6 which is programmed with appropriate software for interpreting the data obtained by the reader device from the diagnostic device. Interpretation of the data from the diagnostic device may be used in a variety of ways, including nucleic acid sequencing which is directed toward a particular disease causing agent, such as viral or bacterial infections, e.g., AIDS, malaria, etc., or genetic disorders, e.g., sickle cell anemia, cystic fibrosis, Fragile X syndrome, Duchenne muscular dystrophy, and the like. Alternatively, the device can be employed in de novo sequencing applications to identify the nucleic acid sequence of a previously unknown sequence.

B. The Diagnostic Device

As described above, the device of the present invention is generally capable of carrying out a number of preparative and analytical reactions on a sample. To achieve this end, the device generally comprises a number of discrete reaction, storage and/or analytical chambers disposed within a single unit or body. While referred to herein as a "diagnostic device," those of skill in the art will appreciate that the device of the invention will have a variety of applications outside the scope of diagnostics, alone. Such applications include sequencing applications, sample identification and characterization applications (for, e.g., taxonomic studies, forensic applications, i.e., criminal investigations, and the like).

Typically, the body of the device defines the various reaction chambers and fluid passages in which the above described operations are carried out. Fabrication of the body, and thus the various chambers and channels disposed within the body may generally be carried out using one or a combination of a variety of well known manufacturing techniques and materials. Generally, the material from which the body is fabricated will be selected so as to provide maximum resistance to the full range of conditions to which the device will be exposed, e.g., extremes of temperature, salt, pH, application of electric fields and the like, and will also be selected for compatibility with other materials used in the device. Additional components may be later introduced, as necessary, into the body. Alternatively, the device may be formed from a plurality of distinct parts that are later assembled or mated. For example, separate and individual chambers and fluid passages may be assembled to provide the various chambers of the device.

As a miniaturized device, the body of the device will typically be approximately 1 to 10 cm in length by about 1 to 10 cm in width by about 0.2 to about 2 cm thick. Although indicative of a rectangular shape, it will be readily appreciated that the devices of the invention may be embodied in any number of shapes depending upon the particular need. Additionally, these dimensions will typically vary depending upon the number of operations to be performed by the device, the complexity of these operations and the like. As a result, these dimensions are provided as a general indication of the size of the device. The number and size of the reaction chambers included within the device will also vary depending upon the specific application for which the device is to be used. Generally, the device will include at least two distinct reaction chambers, and preferably, at least three, four or five distinct reaction chambers, all integrated within a single body. Individual reaction chambers will also vary in size according to the specific function of the reaction chamber. In general however, the reaction chambers will be from about 0.5 to about 20 mm in width or diameter and about 0.05 to about 5 mm deep. Fluid channels, on the other hand, typically range from about 20 to about 1000 $\mu$m wide, preferably, 100 to 500 $\mu$m wide and about 5 to 100 $\mu$m deep.

As described above, the body of the device is generally fabricated using one or more of a variety of methods and materials suitable for microfabrication techniques. For example, the body of the device may comprise a number of planar members that may individually be injection molded parts fabricated from a variety of polymeric materials, or may be silicon, glass, or the like. In the case of crystalline substrates like silica, glass or silicon, methods for etching, milling, drilling, etc. may be used to produce wells and depressions which make up the various reaction chambers and fluid channels within the device. Microfabrication techniques, such as those regularly used in the semiconductor and microelectronics industries are particularly suited to these materials and methods. These techniques include, e.g., electrodeposition, low-pressure vapor deposition, photolithography, etching, laser drilling, and the like. Where these methods are used, it will generally be desirable to fabricate the planar members of the device from materials similar to those used in the semiconductor industry, i.e., silica, silicon or gallium arsenide substrates. U.S. Pat. No. 5,252,294, to Kroy, et al., incorporated herein by reference in its entirety for all purposes, reports the fabrication of a silicon based multiwell apparatus for sample handling in biotechnology applications.

Photolithographic methods of etching substrates are particularly well suited for the microfabrication of hese substrates and are well known in the art. For example, the first sheet of a substrate may be overlaid with a photoresist. An electromagnetic radiation source may then be shone through a photolithographic mask to expose the photoresist in a pattern which reflects the pattern of chambers and/or channels on the surface of the sheet. After removing the exposed photoresist, the exposed substrate may be etched to produce the desired wells and channels. Generally preferred photoresists include those used extensively in the semiconductor industry. Such materials include polymethyl methacrylate (PMMA) and its derivatives, and electron beam resists such as poly(olefin sulfones) and the like (more fully discussed in, e.g., Ghandi, "*VLSI Fabrication Principles,*" Wiley (1983) Chapter 10, incorporated herein by reference in its entirety for all purposes).

As an example, the wells manufactured into the surface of one planar member make up the various reaction chambers of the device. Channels manufactured into the surface of this or another planar member make up fluid channels which are used to fluidly connect the various reaction chambers. Another planar member is then placed over and bonded to the first, whereby the wells in the first planar member define cavities within the body of the device which cavities are the various reaction chambers of the device. Similarly, fluid channels manufactured in the surface of one planar member, when covered with a second planar member define fluid passages through the body of the device. These planar members are bonded together or laminated to produce a fluid tight body of the device. Bonding of the planar members of the device may generally be carried out using a variety of methods known in the art and which may vary depending upon the materials used. For example, adhesives may generally be used to bond the planar members together. Where the planar members are crystalline, e.g., glass or silicon, thermal bonding techniques may be applied. For plastic parts, acoustic welding techniques are generally preferred.

Although primarily described in terms of producing a fully integrated body of the device, the above described methods can also be used to fabricate individual discrete components of the device which are later assembled into the body of the device.

In additional embodiments, the body may comprise a combination of materials and manufacturing techniques described above. In some cases, the body may include some parts of injection molded plastics, and the like, while other portions of the body may comprise etched silica or silicon planar members, and the like. For example, injection molding techniques may be used to form a number of discrete cavities in a planar surface which define the various reaction chambers, whereas additional components, e.g., fluid channels, arrays, etc, may be fabricated on a planar glass, silica or silicon chip or substrate. Lamination of one set of parts to the other will then result in the formation of the various reaction chambers, interconnected by the appropriate fluid channels.

In particularly preferred embodiments, the body of the device is made from at least one injection molded, press molded or machined polymeric part that has one or more wells or depressions manufactured into its surface to define several of the walls of the reaction chamber or chambers. Examples of suitable polymers for injection molding or machining include, e.g., polycarbonate, polystyrene, polypropylene, polyethylene acrylic, and commercial polymers such as Kapton, Valox, Teflon, ABS, Delrin and the like. A second part that is similarly planar in shape is mated to the surface of the polymeric part to define the remaining wall of the reaction chamber(s). U.S. patent application Ser. No. 08/528,173, filed Sep. 15, 1995, incorporated herein by reference, describes a device that is used to package individual oligonucleotide arrays. The device includes a hybridization chamber disposed within a planar body. The chamber is fluidly connected to an inlet port and an outlet port via flow channels in the body of the device. The body includes a plurality of injection molded planar parts that are mated to form the body of the device, and which define the flow channels and hybridization chamber.

Figure 2A:
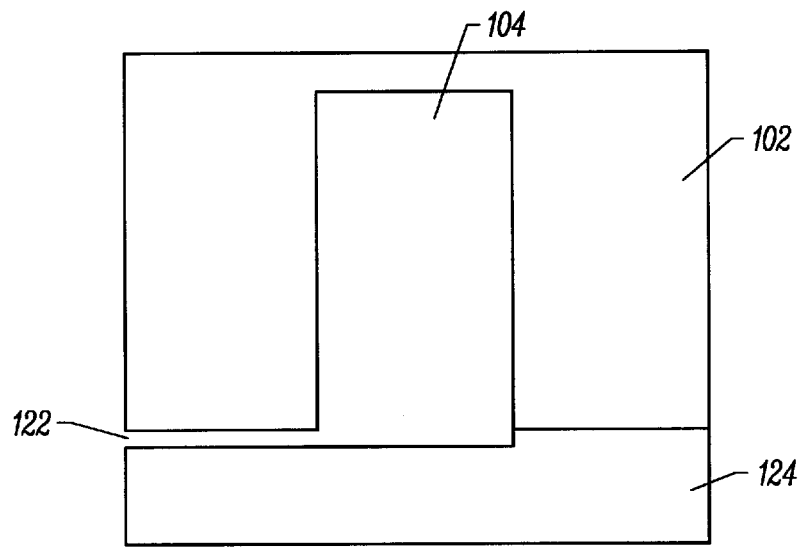
FIGS. 2A and 2B show schematic representations of two alternate reaction chamber designs from a cut-away view.
Figure 2B:
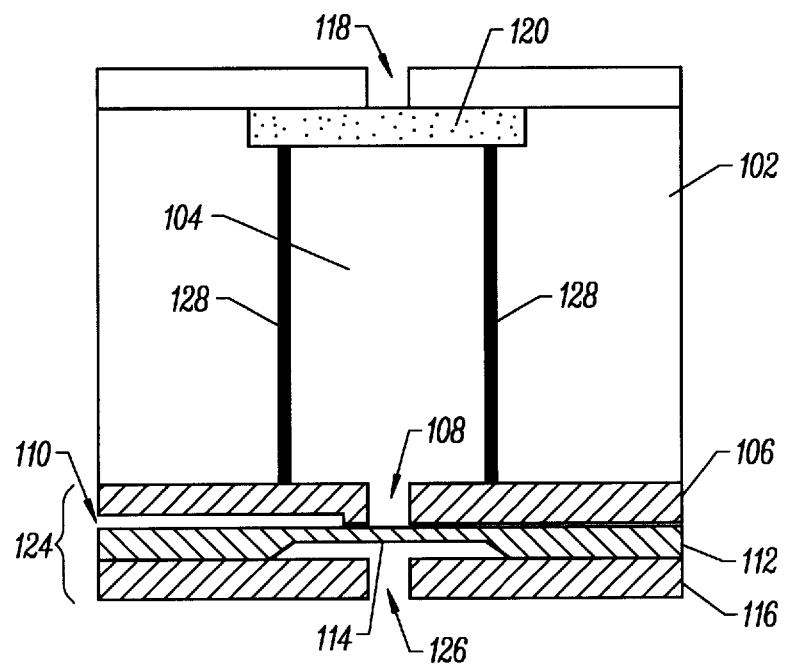

FIGS. 2A and 2B show a schematic representation of one embodiment of a reaction chamber for inclusion in the device of the invention. The reaction chamber includes a machined or injection molded polymeric part 102 which has a well 104 manufactured, i.e., machined or molded, into its surface. This well may be closed at the end opposite the well opening as shown in FIG. 2A, or optionally, may be supplied with an additional opening 118 for inclusion of an optional vent, as shown in FIG. 2B.

The reaction chamber is also provided with additional elements for transporting a fluid sample to and from the reaction chamber. These elements include one or more fluid channels (122 and 110 in FIGS. 2A and 2B, respectively) which connect the reaction chamber to an inlet/outlet port for the overall device, additional reaction chambers, storage chambers or one or more analytical chambers.

A second part 124, typically planar in structure, is mated to the polymeric part to define a closure for the reaction chamber. This second part may incorporate the fluid channels, as shown in FIGS. 2A and 2B, or may merely define a further wall of the fluid channels provided in the surface of the first polymeric part (not shown). Typically, this second part will comprise a series of fluid channels manufactured into one of its surfaces, for fluidly connecting the reaction chamber to an inlet port in the overall device or to another reaction or analytical chamber. Again, this second part may be a second polymeric part made by injection molding or machining techniques. Alternatively, this second part may be manufactured from a variety of other materials, including glass, silica, silicon or other crystalline substrates. Microfabrication techniques suited for these substrates are generally well known in the art and are described above.

In a first preferred embodiment, the reaction chamber is provided without an inlet/outlet valve structure, as shown in FIG. 2A. For these embodiments, the fluid channels 122 may be provided in the surface of the second part that is mated with the surface of the polymeric part such that upon mating the second part to the first polymeric part, the fluid channel 122 is fluidly connected to the reaction chamber 104.

Alternatively, in a second preferred embodiment, the reaction chamber may be provided with an inlet/outlet valve structure for sealing the reaction chamber to retain a fluid sample therein. An example of such a valve structure is shown in FIG. 2B. In particular, the second part 124 mated to the polymeric part may comprise a plurality of mated planar members, wherein a first planar member 106 is mated with the first polymeric part 102 to define a wall of the reaction chamber. The first planar member 106 has an opening 108 disposed therethrough, defining an inlet to the reaction chamber. This first planar member also includes a fluid channel 110 etched in the surface opposite the surface that is mated with the first polymeric part 102. The fluid channel terminates adjacent to, but not within the reaction chamber inlet 108. The first planar member will generally be manufactured from any of the above described materials, using the above-described methods. A second planar member 112 is mated to the first and includes a diaphragm valve 114 which extends across the inlet 108 and overlaps with the fluid channel 110 such that deflection of the diaphragm results in a gap between the first and second planar members, thereby creating a fluid connection between the reaction chamber 104 and the fluid channel 110, via the inlet 108. Deflection of the diaphragm valve may be carried out by a variety of methods including, e.g., application of a vacuum, electromagnetic and/or piezoelectric actuators coupled to the diaphragm valve, and the like. To allow for a deflectable diaphragm, the second planar member will typically be fabricated, at least in part, from a flexible material, e.g., silicon, mylar, teflon or other flexible polymers. As with the reaction chambers and fluid channels, these diaphragms will also be of miniature scale. Specifically, valve and pump diaphragms used in the device will typically range in size depending upon the size of the chamber or fluid passage to which they are fluidly connected. In general, however, these diaphragms will be in the range of from about 0.5 to about 5 mm for valve diaphragms, and from about 1 to about 20 mm in diameter for pumping diaphragms. As shown in FIG. 2B, second part 124 includes an additional planar member 116 having an opening 126 for application of a vacuum pressure for deflection of diaphragm 114.

Where reagents involved in a particular analysis are incompatible with the materials used to manufacture the device, e.g., silicon or polymeric parts, a variety of coatings may be applied to the surfaces of these parts that contact these reagents. For example, components that have elements of silicon may be coated with a silicon nitride layer or a metallic layer of, e.g., gold or nickel, may be sputtered or electroplated on the surface to avoid adverse reactions with these reagents. Similarly, inert polymer coatings may also be applied to internal surfaces of the device, e.g., Teflon and the like.

The reaction/storage chamber 104 shown in FIG. 3B is also shown with an optional vent 118, for release of displaced gas present in the chamber when the fluid is introduced. In preferred aspects, this vent may be fitted with a poorly wetting filter plug 120, which permits the passage of gas without allowing for the passage of fluid. A variety of materials are suitable for use as poorly wetting filter plugs including, e.g., porous hydrophobic polymer materials, such as spun fibers of acrylic, polycarbonate, teflon, pressed polypropylene fibers, or any number commercially available filter plugs (American Filtrona Corp., Richmond, Va.). Alternatively, a hydrophobic membrane can be bonded over a thru-hole to supply a similar structure. Modified acrylic copolymer membranes are commercially available from, e.g., Gelman Sciences (Ann Arbor, Mich.) and particle-track etched polycarbonate membranes are available from Poretics, Inc. (Livermore, Calif.). Venting of heated chambers may incorporate barriers to evaporation of the sample, e.g., a reflux chamber or a mineral oil layer disposed within the chamber, and over the top surface of the sample, to permit the evolution of gas while preventing excessive evaporation of fluid from the sample.

As described herein, the overall geometry of the device of the invention may take a number of forms. For example, the device may incorporate a plurality of reaction chambers, storage chambers and analytical chambers, arranged in series, whereby a fluid sample is moved serially through the chambers, and the respective operations performed in these chambers. Alternatively, the device may incorporate a central chamber having the various reaction/storage/analytical chambers arranged around and fluidly connected to the central chamber, which central chamber acts as a sample gathering and redistribution hub for these various chambers.

Figure 3:
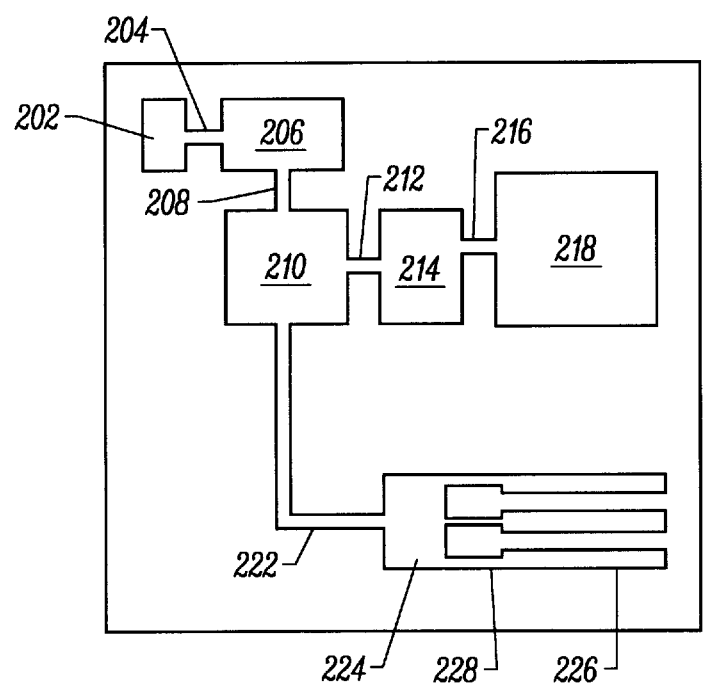
FIG. 3 shows a schematic representation of a miniature integrated diagnostic device having a number of reaction chambers arranged in a serial geometry.

An example of the serial geometry of the device is shown in FIG. 3. In particular, the illustrated device includes a plurality of reaction/storage/analytical chambers for performing a number of the operations described above, fluidly connected in series.

The schematic representation of the device in FIG. 2 shows a device that comprises several reaction chambers arranged in a serial geometry. Specifically, the body of the device 200 incorporates reaction chambers 202, 206, 210, 214 and 218. These chambers are fluidly connected in series by fluid channels 208, 212 and 216, respectively.

In carrying out the various operations outlined above, each of these reaction chambers is assigned one or more different functions. For example, reaction chamber 202 may be a sample collection chamber which is adapted for receiving a fluid sample such as a cell containing sample. For example, this chamber may include an opening to the outside of the device adapted for receipt of the sample. The opening will typically incorporate a sealable closure to prevent leakage of the sample, e.g., a valve, check-valve, or septum, through which the sample is introduced or injected. In some embodiments, the apparatus may include a hypodermic needle integrated into the body of the device and in fluid connection with the sample collection chamber, for direct transfer of the sample from the host, patient, sample vial or tube, or other origin of the sample to the sample collection chamber.

Additionally, the sample collection chamber may have disposed therein, a reagent or reagents for the stabilization of the sample for prolonged storage, as described above. Alternatively, these reagents may be disposed within a reagent storage chamber adjacent to and fluidly connected with the sample collection chamber.

The sample collection chamber is connected via a first fluid channel 204 to second reaction chamber 210 in which the extraction of nucleic acids from the cells within the sample may be performed. This is particularly suited to analytical operations to be performed where the samples include whole cells. The extraction chamber will typically be connected to sample collection chamber, however, in some cases, the extraction chamber may be integrated within and exist as a portion of the sample collection chamber. As previously described, the extraction chamber may include physical and or chemical means for extracting nucleic acids from cells.

The extraction chamber is fluidly connected via a second fluid channel 208, to third reaction chamber 210 in which amplification of the nucleic acids extracted from the sample is carried out. The amplification process begins when the sample is introduced into the amplification chamber. As described previously, amplification reagents may be exogenously introduced, or will preferably be predisposed within the reaction chamber. However, in alternate embodiments, these reagents will be introduced to the amplification chamber from an optional adjacent reagent chamber or from an external source through a sealable opening in the amplification chamber.

For PCR amplification methods, denaturation and hybridization cycling will preferably be carried out by repeated heating and cooling of the sample. Accordingly, PCR based amplification chambers will typically include a a temperature controller for heating the reaction to carry out the thermal cycling. For example, a heating element or temperature control block may be disposed adjacent the external surface of the amplification chamber thereby transferring heat to the amplification chamber. Micro-scale PCR devices have been previously reported. For example, published PCT Application No. WO 94/05414, to Northrup and White reports a miniaturized reaction chamber for use as a PCR chamber, incorporating microheaters, e.g., resistive heaters. The high surface area to volume ratio of the chamber allows for very rapid heating and cooling of the reagents disposed therein. Similarly, U.S. Pat. No. 5,304,487 to Wilding et al., previously incorporated by reference, also discusses the use of a microfabricated PCR device.

In preferred embodiments, the amplification chamber will incorporate a controllable heater disposed within or adjacent to the amplification chamber, for thermal cycling of the sample. Thermal cycling is carried out by varying the current supplied to the heater to achieve the desired temperature for the particular stage of the reaction. Alternatively, thermal cycling for the PCR reaction may be achieved by transferring the fluid sample among a number of different reaction chambers or regions of the same reaction chamber, having different, although constant temperatures, or by flowing the sample through a serpentine channel which travels through a number of varied temperature 'zones'. Heating may alternatively be supplied by exposing the amplification chamber to a laser or other light or electromagnetic radiation source.

The amplification chamber is fluidly connected via a fluid channel, e.g., fluid channel 212, to an additional reaction chamber 214 which can carry out additional preparative operations, such as labeling or fragmentation.

A fourth fluid channel 216 connects the labeling or fragmentation chamber to an analytical chamber 218. As shown, the analytical chamber includes an oligonucleotide array 220 as the bottom surface of the chamber. Analytical chamber 218 may optionally, or additionally comprise a microcapillary electrophoresis device and additional preparative reaction chambers for performing, e.g., extension reactions. The analytical chamber will typically have as at least one surface, a transparent window for observation or scanning of the particular analysis being performed.

Figure 4A:
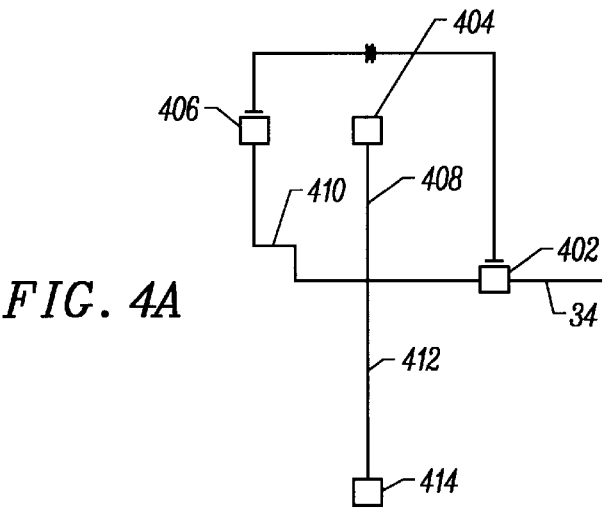
FIGS. 4A–C show a representation of a microcapillary electrophoresis device.
Figure 4B:
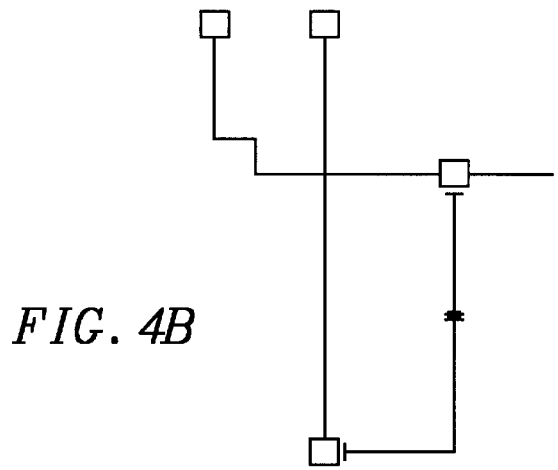
Figure 4C:
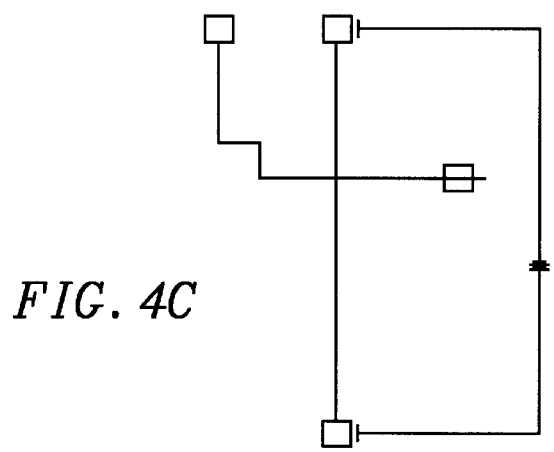

FIGS. 4A–C illustrate an embodiment of a microcapillary electrophoresis device. In this embodiment, the sample to be analyzed is introduced into sample reservoir 402. This sample reservoir may be a separate chamber, or may be merely a portion of the fluid channel leading from a previous reaction chamber. Reservoirs 404, 406 and 414 are filled with sample/running buffer. FIG. 4A illustrates the loading of the sample by plug loading, where the sample is drawn across the intersection of loading channel 416 and capillary channel 412, by application of an electrical current across buffer reservoir 406 and sample reservoir 402. In alternative embodiments, the sample is "stack" loaded by applying an electrical current across sample reservoir 402 and waste reservoir 414, as shown in FIG. 4B. Following sample loading, an electrical field is applied across buffer reservoir 404 and waste reservoir 414, electrophoresing the sample through the capillary channel 412. Running of the sample is shown in FIG. 4C. Although only a single capillary is shown in FIGS. 4A–C, the device of the present invention may typically comprise more than one capillary, and more typically, will comprise an array of four or more capillaries, which are run in parallel. Fabrication of the microcapillary electrophoresis device may generally be carried using the methods described herein and as described in e.g., Woolley and Mathies, Proc. Nat'l Acad. Sci. USA 91:11348–11352 (1994), incorporated herein by reference in its entirety for all purposes. Typically, each capillary will be fluidly connected to a separate extension reaction chamber for incorporation of a different dideoxynucleotide.

An alternate layout of the reaction chambers within the device of the invention, as noted above, includes a centralized geometry having a central chamber for gathering and distribution of a fluid sample to a number of separate reaction/storage/analytical chambers arranged around, and fluidly connected to the central chamber. An example of this centralized geometry is shown in FIG. 5. In the particular device shown, a fluid sample is introduced into the device through sample inlet 502, which is typically fluidly connected to a sample collection chamber 504. The fluid sample is then transported to a central chamber 508 via fluid channel 506. Once within the central chamber, the sample may be transported to any one of a number of reaction/storage/analytical chambers (510, 512, 514) which are arranged around and fluidly connected to the central chamber. As shown, each of reaction chambers 510, 512 and 514, includes a diaphragm 516, 518 and 520, respectively, as shown in FIG. 2B, for opening and closing the fluid connection between the central chamber 508 and the reaction chamber. Additional reaction chambers may be added fluidly connected to the central chamber, or alternatively, may be connected to any of the above described reaction chambers, as indicated by arrows 522.

In preferred aspects, the central chamber has a dual function as both a hub and a pumping chamber. In particular, this central pumping chamber is typically fluidly connected to one or more additional reaction and/or storage chambers and one or more analytical chambers. The central pumping chamber again functions as a hub for the various operations to be carried out by the device as a whole as described above. This embodiment provides the advantage of a single pumping chamber to deliver a sample to numerous operations, as well as the ability to readily incorporate additional sample preparation operations within the device by opening another valve on the central pumping chamber.

In particular, the central chamber 508 typically incorporates a diaphragm pump as one surface of the chamber, and in preferred aspects, will have a zero displacement when the diaphragm is not deflected. The diaphragm pump will generally be similar to the valve structure described above for the reaction chamber. For example, the diaphragm pump will generally be fabricated from any one of a variety of flexible materials, e.g., silicon, latex, teflon, mylar and the like. In particularly preferred embodiments, the diaphragm pump is silicon.

Figure 5A:
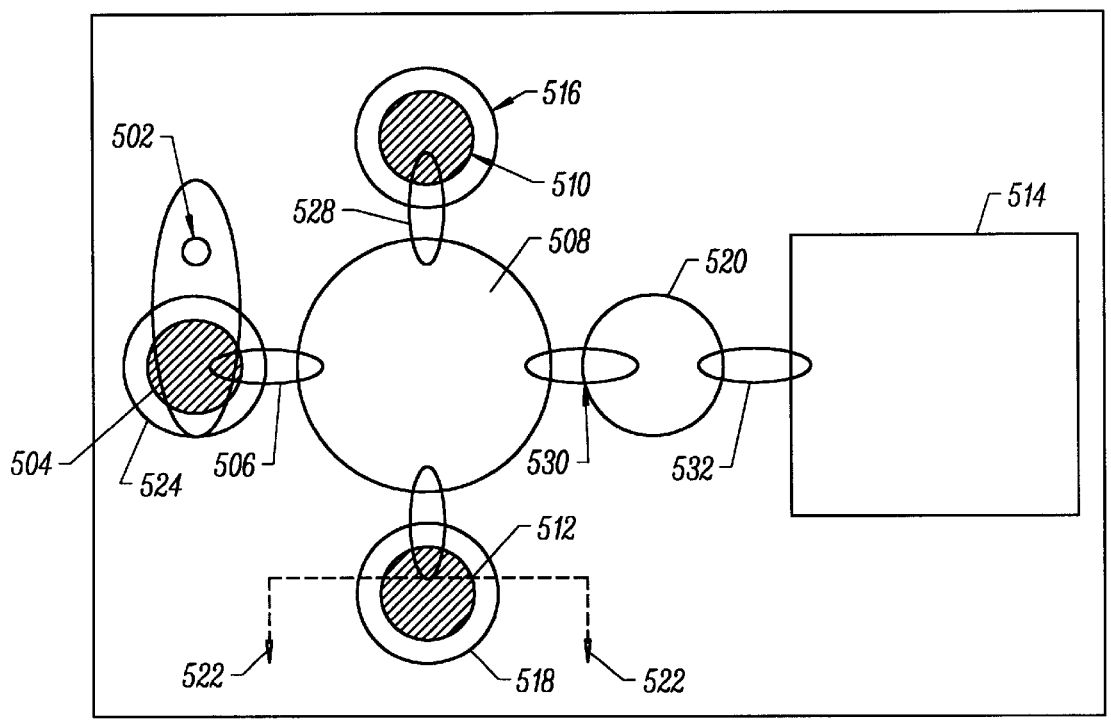
FIG. 5A illustrates a top view of a miniature integrated device which employs a centralized geometry.
Figure 5B:
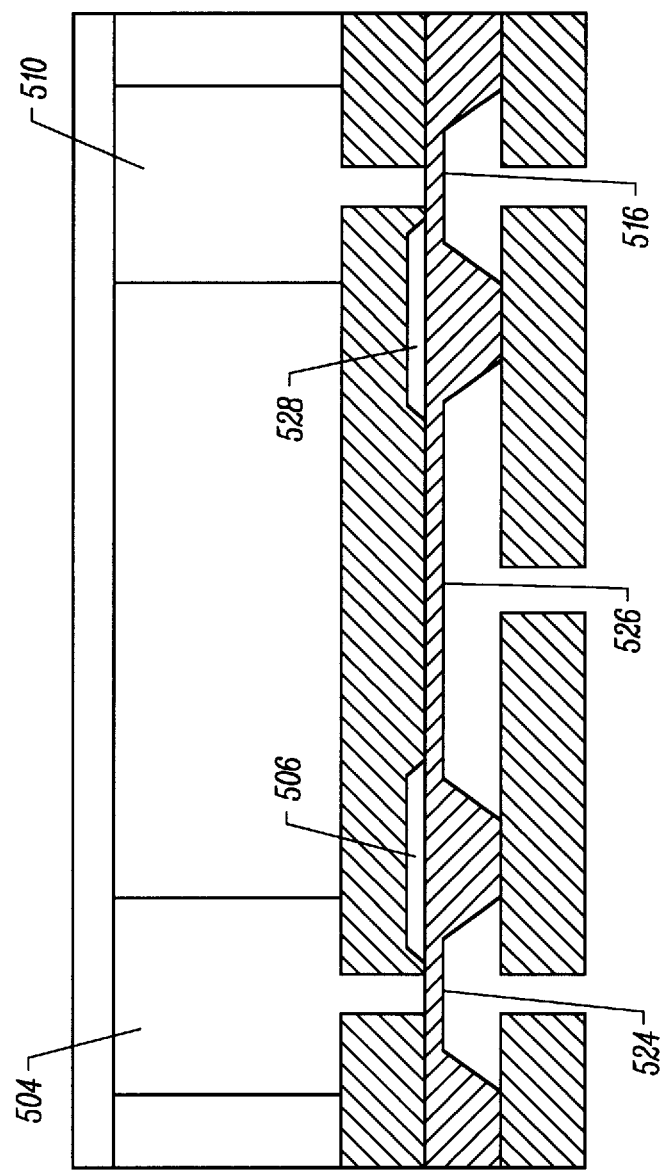
FIG. 5B shows a side view of the same device wherein the central chamber is a pumping chamber, and employing diaphragm valve structures for sealing reaction chambers.

With reference to both FIGS. 5A and 5B, central chamber 508 is fluidly connected to sample collection chamber 504, via fluid channel 506. The sample collection chamber end of fluid channel 506 includes a diaphragm valve 524 for arresting fluid flow. A fluid sample is typically introduced into sample collection chamber through a sealable opening 502 in the body of the device, e.g., a valve or septum. Additionally, sample chamber 504 may incorporate a vent to allow displacement of gas or fluid during sample introduction.

Once the sample is introduced into the sample collection chamber, it may be drawn into the central pumping chamber 508 by the operation of pump diaphragm 526. Specifically, opening of sample chamber valve 524 opens fluid channel 506. Subsequent pulling or deflection of pump diaphragm 526 creates negative pressure within pumping chamber 508, thereby drawing the sample through fluid channel 506 into the central chamber. Subsequent closing of the sample chamber valve 524 and relaxation of pump diaphragm 526, creates a positive pressure within pumping chamber 508, which may be used to deliver the sample to additional chambers in the device. For example, where it is desired to add specific reagents to the sample, these reagents may be stored in liquid or solid form within an adjacent storage chamber 510. Opening valve 516 opens fluid channel 528, allowing delivery of the sample into storage chamber 510 upon relaxation of the diaphragm pump. The operation of pumping chamber may further be employed to mix reagents, by repeatedly pulling and pushing the sample/reagent mixture to and from the storage chamber. This has the additional advantage of eliminating the necessity of including additional mixing components within the device. Additional chamber/valve/fluid channel structures may be provided fluidly connected to pumping chamber 508 as needed to provide reagent storage chambers, additional reaction chambers or additional analytical chambers. FIG. 5A illustrates an additional reaction/storage chamber 514 and valve 520, fluidly connected to pumping chamber 508 via fluid channel 530. This will typically vary depending upon the nature of the sample to be analyzed, the analysis to be performed, and the desired sample preparation operation. Following any sample preparation operation, opening valve 520 and closure of other valves to the pumping chamber, allows delivery of the sample through fluid channels 530 and 532 to reaction chamber 514, which may include an analytical device such as an oligonucleotide array for determining the hybridization of nucleic acids in the sample to the array, or a microcapillary electrophoresis device for performing a size based analysis of the sample.

The transportation of fluid within the device of the invention may be carried out by a number of varied methods. For example, fluid transport may be affected by the application of pressure differentials provided by either external or internal sources. Alternatively, internal pump elements which are incorporated into the device may be used to transport fluid samples through the device.

In a first embodiment, fluid samples are moved from one reaction/storage/analytical chamber to another chamber via fluid channels by applying a positive pressure differential from the originating chamber, the chamber from which the sample is to be transported, to the receiving chamber, the chamber to which the fluid sample is to be transported. In order to apply the pressure differentials, the various reaction chambers of the device will typically incorporate pressure inlets connecting the reaction chamber to the pressure source (positive or negative). For ease of discussion, the application of a negative pressure, i.e., to the receiving chamber, will generally be described herein. However, upon reading the instant disclosure, one of ordinary skill in the art will appreciate that application of positive pressure, i.e., to the originating chamber, will be as effective, with only slight modifications, which will be illustrated as they arise herein.

In one method, application of the pressure differential to a particular reaction chamber may generally be carried out by selectively lowering the pressure in the receiving chamber. Selective lowering of the pressure in a particular receiving chamber may be carried out by a variety of methods. For example, the pressure inlet for the reaction chambers may be equipped with a controllable valve structure which may be selectively operated to be opened to the pressure source. Application of the pressure source to the sample chamber then forces the sample into the next reaction chamber which is at a lower pressure.

Typically, the device will include a pressure/vacuum manifold for directing an external vacuum source to the various reaction/storage/analytical chambers. A particularly elegant example of a preferred vacuum pressure manifold is illustrated in FIGS. 6A, 6B and 6C.

The vacuum/pressure manifold produces a stepped pressure differential between each pair of connected reaction chambers. For example, assuming ambient pressure is defined as having a value of 1, a vacuum is applied to a first reaction chamber, which may be written 1–3x, where x is an incremental pressure differential. A vacuum of 1–2x is applied to a second reaction chamber in the series, and a vacuum of 1–x is applied to a third reaction chamber. Thus, the first reaction chamber is at the lowest pressure and the third is at the highest, with the second being at an intermediate level. All chambers, however, are below ambient pressure, e.g., atmospheric. The sample is drawn into the first reaction chamber by the pressure differential between ambient pressure (1) and the vacuum applied to the reaction chamber (1–3x), which differential is –3x. The sample does not move to the second reaction chamber due to the pressure differential between the first and second reaction chambers (1–3x vs. 1–2x, respectively). Upon completion of the operation performed in the first reaction chamber, the vacuum is removed from the first chamber, allowing the first chamber to come to ambient pressure, e.g., 1. The sample is then drawn from the first chamber into the second by the pressure difference between the ambient pressure of the first reaction chamber and the vacuum of the second chamber, e.g., 1 vs. 12x. Similarly, when the operation to be performed in the second reaction chamber is completed, the vacuum to this chamber is removed and the sample moves to the third reaction chamber.

Figure 6A:
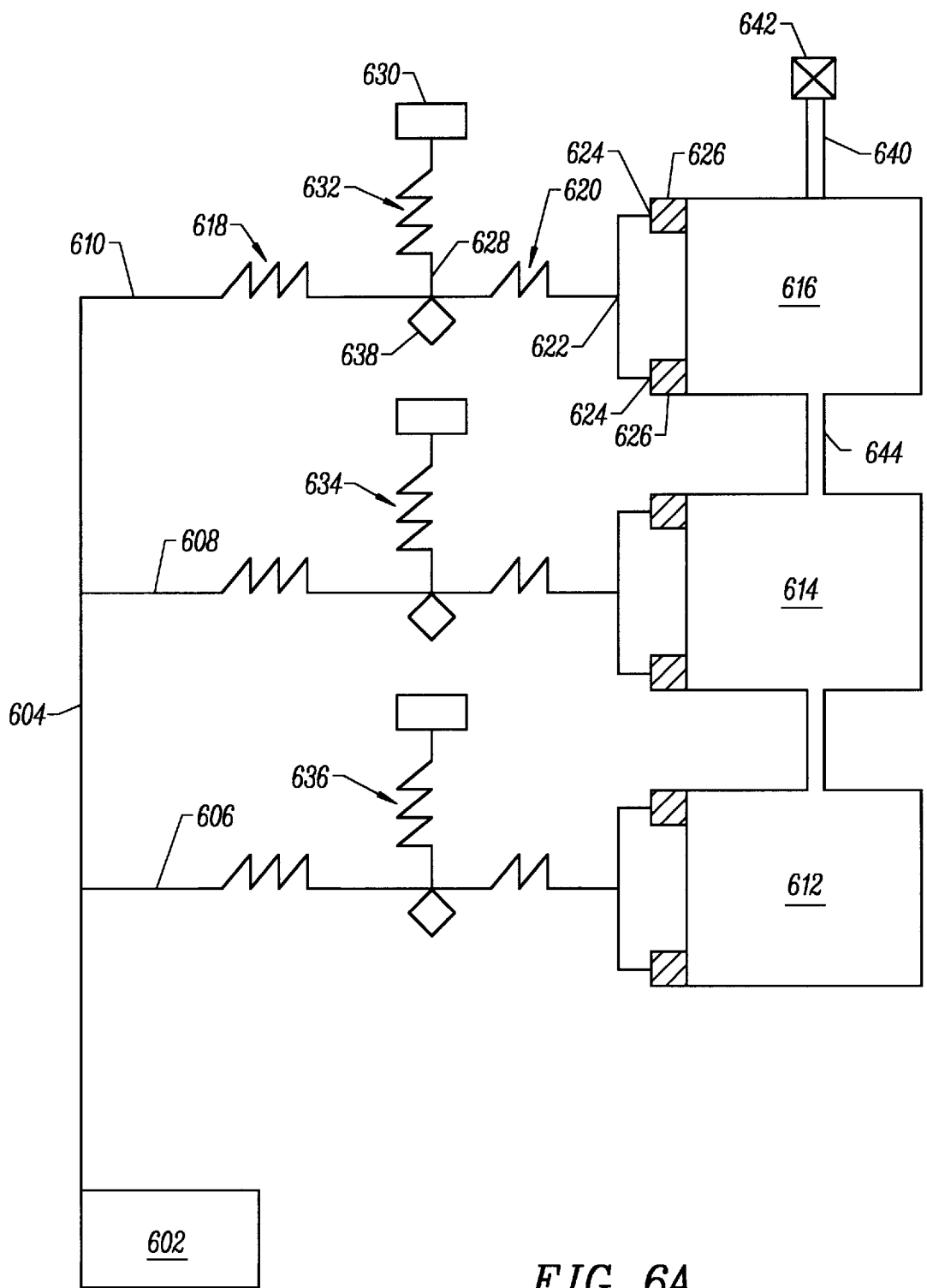
Figure 6B:
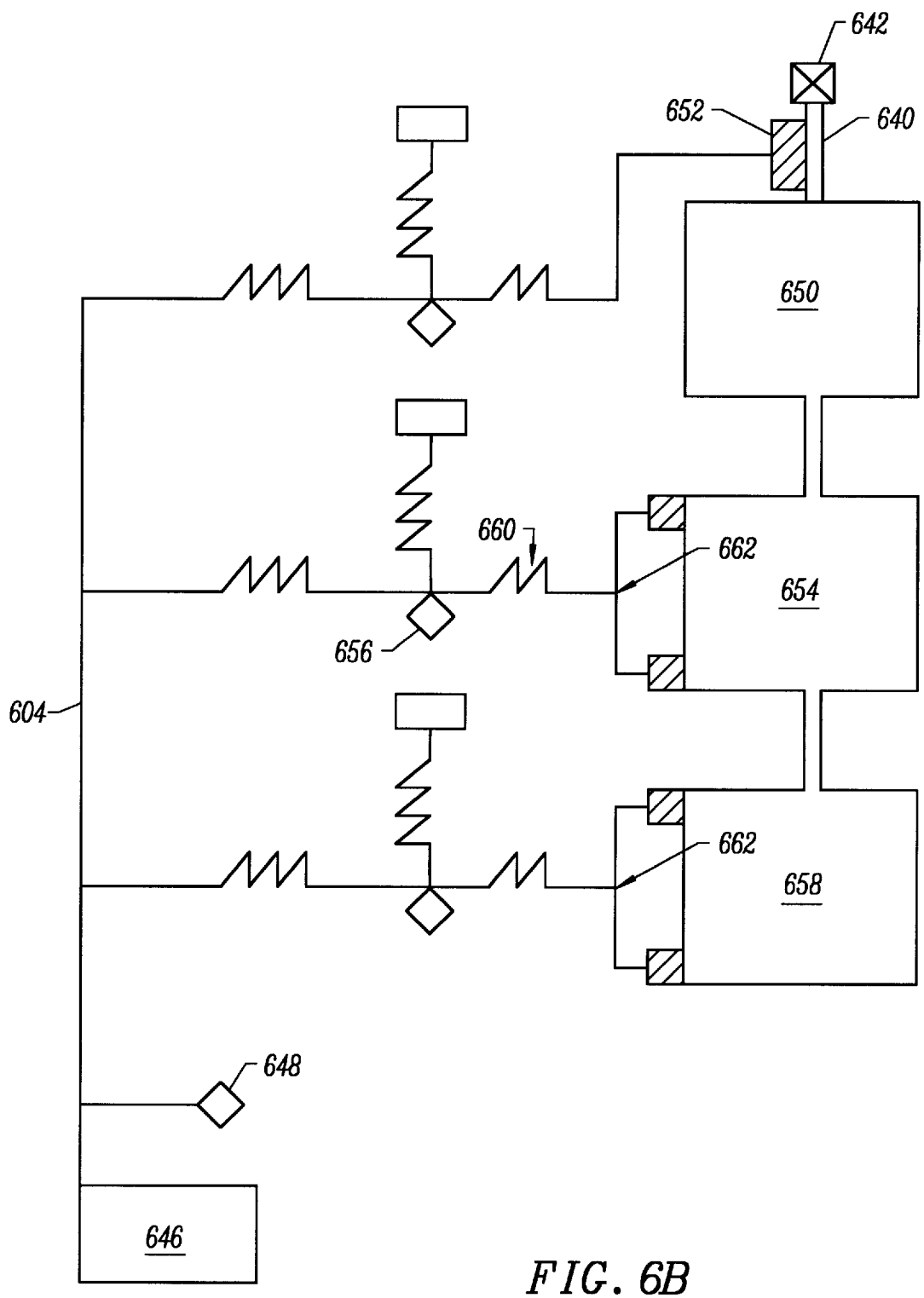
FIG. 6B shows a manifold configuration for application of positive pressures.
Figure 6C:
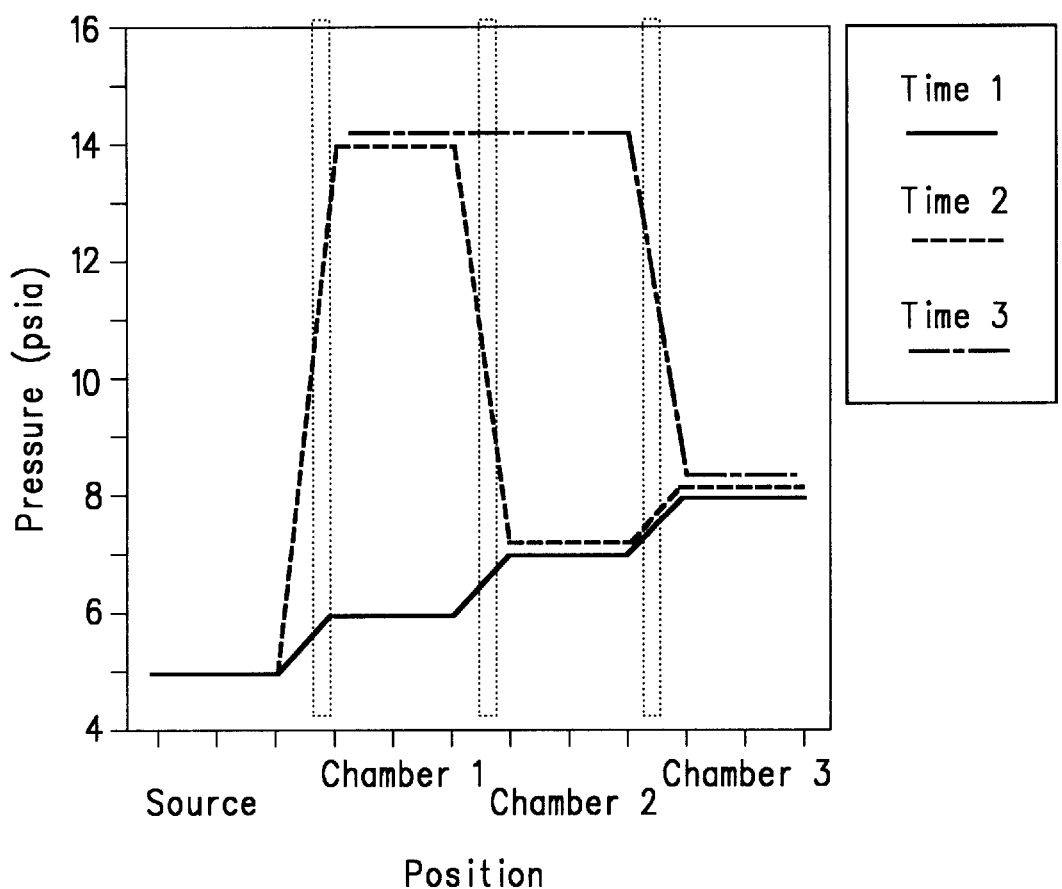
FIG. 6C illustrates a pressure profile for moving fluids among several reaction chambers.

A schematic representation of a pneumatic manifold configuration for carrying out this pressure differential fluid transport system is shown in FIG. 6A. The pneumatic manifold includes a vacuum source 602 which is coupled to a main vacuum channel 604. The main vacuum channel is connected to branch channels 606, 608 and 610, which are in turn connected to reaction chambers 612, 614 and 616, respectively, which reaction chambers are fluidly connected, in series. The first reaction chamber in the series 616 typically includes a sample inlet 640 which will typically include a sealable closure for retaining he fluid sample and the pressure within the reaction chamber. Each branch channel is provided with one or more fluidic resistors 618 and 620 incorporated within the branch channel. These fluidic resistors result in a transformation of the pressure from the pressure/vacuum source, i.e., a step down of the gas pressure or vacuum being applied across the resistance. Fluidic resistors may employ a variety of different structures. For example, a narrowing of the diameter or cross-sectional area of a channel will typically result in a fluidic resistance through the channel. Similarly, a plug within the channel which has one or more holes disposed therethrough, which effectively narrow the channel through which the pressure is applied, will result in a fluidic resistance, which resistance can be varied depending upon the number and/or size of the holes in the plug. Similarly, the plug may be fabricated from a porous material which provides a fluidic resistance through the plug, which resistance may be varied depending upon the porosity of the material and/or the number of plugs used.

Each branch channel will typically be connected at a pressure node 622 to the reaction chamber via pressure inlets 624. Pressure inlets 624 will typically be fitted with poorly wetting filter plugs 626, to prevent drawing of the sample into the pneumatic manifold in the case of vacuum based methods. Poorly wetting filter plugs may generally be prepared from a variety of materials known in the art and as described above. Each branch channel is connected to a vent channel 628 which is opened to ambient pressure via vent 630. A differential fluidic resistor 632 is incorporated into vent channel 628. The fluidic resistance supplied by fluidic resistor 632 will be less than fluidic resistance supplied by fluidic resistor 634 which will be less than fluidic resistance supplied by fluidic resistor 636. As described above, this differential fluidic resistance may be accomplished by varying the diameter of the vent channel, varying the number of channels included in a single vent channel, or providing a plug in the vent channel having a varied number of holes disposed therethrough.

The varied fluidic resistances for each vent channel will result in a varied level of vacuum being applied to each reaction chamber, where, as described above, reaction chamber 616 may have a pressure of 1–3x, reaction chamber 614 may have a pressure of 1–2x and reaction chamber 612 may have a pressure of 1-x. The pressure of a given reaction chamber may be raised to ambient pressure, thus allowing the drawing of the sample into the subsequent chamber, by opening the chamber to ambient pressure. This is typically accomplished by providing a sealable opening 638 to ambient pressure in the branch channel. This sealable opening may be a controllable valve structure, or alternatively, a rupture membrane which may be pierced at a desired time to allow the particular reaction chamber to achieve ambient pressure, thereby allowing the sample to be drawn into the subsequent chamber. Piercing of the rupture membrane may be carried out by the inclusion of solenoid operated pins incorporated within the device, or the device's base unit (discussed in greater detail below). In some cases, it may be desirable to prevent back flow from a previous or subsequent reaction chamber which is at a higher pressure. This may be accomplished by equipping the fluid channels between the reaction chambers 644 with one-way check valves. Examples of one-way valve structures include ball and seat structures, flap valves, duck billed check valves, sliding valve structures, and the like.

A graphical illustration of the pressure profiles between three reaction chambers employing a vacuum based pneumatic manifold is shown in FIG. 6C. The solid line indicates the starting pressure of each reaction chamber/pressure node. The dotted line indicates the pressure profile during operation. The piercing of a rupture membrane results in an increase in the pressure of the reaction chamber to ambient pressure, resulting in a pressure drop being created between the particular chamber and the subsequent chamber. This pressure drop draws the sample from the first reaction chamber to the subsequent reaction chamber.

In a similar aspect, a positive pressure source may be applied to the originating chamber to push the sample into subsequent chambers. A pneumatic pressure manifold useful in this regard is shown in FIG. 6B. In this aspect, a pressure source 646 provides a positive pressure to the main channel 604. Before a sample is introduced to the first reaction chamber, controllable valve 648 is opened to vent the pressure from the pressure source and allow the first reaction chamber in the series 650 to remain at ambient pressure for the introduction of the sample. Again, the first chamber in the series typically includes a sample inlet 640 having a sealable closure 642. After the sample is introduced into the first reaction chamber 650, controllable valve 648 is closed, bringing the system up to pressure. Suitable controllable valves include any number of a variety of commercially available solenoid valves and the like. In this application, each subsequent chamber is kept at an incrementally higher pressure by the presence of the appropriate fluidic resistors and vents, as described above. A base pressure is applied at originating pressure node 652. When it is desired to deliver the sample to the second chamber 654, sealable opening 656 is opened to ambient pressure. This allows second chamber 654, to come to ambient pressure, allowing the pressure applied at the origin pressure node 652 to force the sample into the second chamber 654. Thus, illustrated as above, the first reaction chamber 650 is maintained at a pressure of 1+x, by application of this pressure at originating pressure node 652. The second reaction chamber 654 is maintained at pressure 1+2x and the third reaction chamber 658 is maintained at a pressure of 1+3x. Opening sealable valve 656 results in a drop in the pressure of the second reaction chamber 654 to 1 (or ambient pressure). The pressure differential from the first to the second reaction chamber, x, pushes the sample from the first to the second reaction chamber and eventually to the third. Fluidic resistor 660 is provided between pressure node 662 and sealable valve 656 to prevent the escape of excess pressure when sealable valve 656 is opened. This allows the system to maintain a positive pressure behind the sample to push it into subsequent chambers.

In a related aspect, a controllable pressure source may be applied to the originating reaction vessel to push a sample through the device. The pressure source is applied intermittently, as needed to move the sample from chamber to chamber. A variety of devices may be employed in applying an intermittent pressure to the originating reaction chamber, e.g., a syringe or other positive displacement pump, or the like. Alternatively, for the size scale of the device, a thermopneumatic pump may be readily employed. An example of such a pump typically includes a heating element, e.g., a small scale resistive heater disposed in a pressure chamber. Also disposed in the chamber is a quantity of a controlled vapor pressure fluid, such as a fluorinated hydrocarbon liquid, e.g., fluorinert liquids available from 3M Corp. These liquids are commercially available having a wide range of available vapor pressures. An increase in the controllable temperature of the heater increases pressure in the pressure chamber, which is fluidly connected to the originating reaction chamber. This increase in pressure results in a movement of the sample from one reaction chamber to the next. When the sample reaches the subsequent reaction chamber, the temperature in the pressure chamber is reduced.

A number of the operations performed by the various reaction chambers of the device require a controllable temperature. For example, PCR amplification, as described above, requires cycling of the sample among a strand separation temperature, an annealing reaction temperature and an extension reaction temperature. A number of other reactions, including extension, transcription and hybridization reactions are also generally carried out at optimized, controlled temperatures. Temperature control within the device of the invention is generally supplied by thin film resistive heaters which are prepared using methods that are well known in the art. For example, these heaters may be fabricated from thin metal films applied within or adjacent to a reaction chamber using well known methods such as sputtering, controlled vapor deposition and the like. The thin film heater will typically be electrically connected to a power source which delivers a current across the heater. The electrical connections will also be fabricated using methods similar to those described for the heaters.

Typically, these heaters will be capable of producing temperatures in excess of 100 degrees without suffering adverse effects as a result of the heating. Examples of resistor heaters include, e.g., the heater discussed in Published PCT Application No. WO 94/05414, laminated thin film Nicr/polyimide/copper heaters, as well as graphite heaters. These heaters may be provided as a layer on one surface of a reaction chamber, or may be provided as molded or machined inserts for incorporation into the reaction chambers. FIG. 2B illustrates an example of a reaction chamber 104 having a heater insert 128, disposed therein. The resistive heater is typically electrically connected to a controlled power source for applying a current across the heater. Control of the power source is typically carried out by an appropriately programmed computer. The above-described heaters may be incorporated within the individual reaction chambers by depositing a resistive metal film or insert within the reaction chamber, or alternatively, may be applied to the exterior of the device, adjacent to the particular reaction chamber, whereby the heat from the heater is conducted into the reaction chamber.

Temperature controlled reaction chambers will also typically include a miniature temperature sensor for monitoring the temperature of the chamber, and thereby controlling the application of current across the heater. A wide variety of microsensors are available for determining temperatures, including, e.g., thermocouples having a bimetallic junction which produces a temperature dependent electromotive force (EMF), resistance thermometers which include material having an electrical resistance proportional to the temperature of the material, thermistors, IC temperature sensors, quartz thermometers and the like. See, Horowitz and Hill, The Art of Electronics, Cambridge University Press 1994 (2nd Ed. 1994). One heater/sensor design that is particularly suited to the device of the present invention is described in, e.g., U.S. patent application Ser. No. 08/535,875, filed Sep. 28, 1995, and incorporated herein by reference in its entirety for all purposes. Control of reaction parameters within the reaction chamber, e.g., temperature, may be carried out manually, but is preferably controlled via an appropriately programmed computer. In particular, the temperature measured by the temperature sensor and the input for the power source will typically be interfaced with a computer which is programmed to receive and record this data, i.e., via an analog-digital/digital-analog (AD/DA) converter. The same computer will typically include programming for instructing the delivery of appropriate current for raising and lowering the temperature of the reaction chamber. For example, the computer may be programmed to take the reaction chamber through any number of predetermined time/temperature profiles, e.g., thermal cycling for PCR, and the like. Given the size of the devices of the invention, cooling of the reaction chambers will typically occur through exposure to ambient temperature, however additional cooling elements may be included if desired, e.g., coolant systems, peltier coolers, water baths, etc.

In addition to fluid transport and temperature control elements, one or more of the reaction chambers of the device may also incorporate a mixing function. For a number of reaction chambers, mixing may be applied merely by pumping the sample back and forth into and out of a particular reaction chamber. However, in some cases constant mixing within a single reaction/analytical chamber is desired, e.g., PCR amplification reactions and hybridization reactions.

Figure 7A:
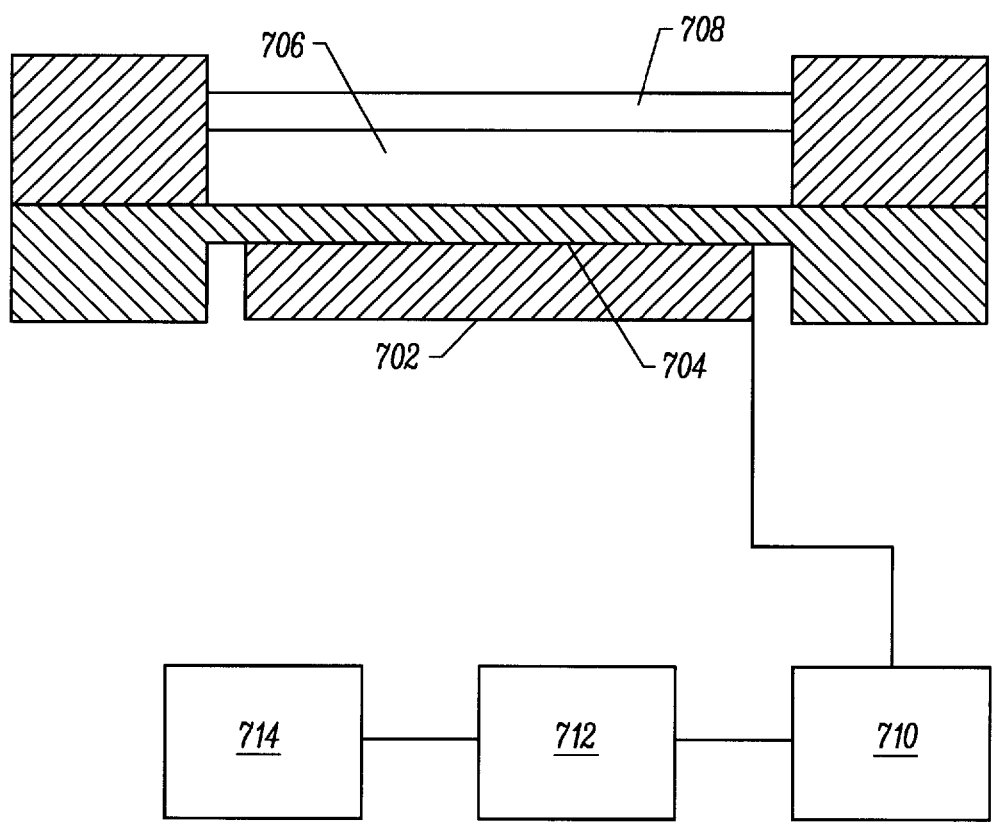
FIG. 7A shows a schematic illustration of a reaction chamber incorporating a PZT element for use in mixing the contents of the reaction chamber.

In preferred aspects, acoustic mixing is used to mix the sample within a given reaction chamber. In particular, a PZT element (element composed of lead, zirconium and titanium containing ceramic) is contacted with the exterior surface of the device, adjacent to the reaction chamber, as shown in FIG. 7A. For a discussion of PZT elements for use in acoustic based methods, see, Physical Acoustics, Principles and Methods, Vol. I, (Mason ed., Academic Press, 1965), and Piezoelectric Technology, Data for Engineers, available from Clevite Corp. As shown, PZT element 702 is contacting the external surface 704 of hybridization chamber 706. The hybridization chamber includes as one internal surface, an oligonucleotide array 708. Application of a current to this element generates sonic vibrations which are translated to the reaction chamber whereupon mixing of the sample disposed therein occurs. The vibrations of this element result in substantial convection being generated within the reaction chamber. A symmetric mixing pattern generated within a micro reaction chamber incorporating this mixing system is shown FIG. 7B.

Incomplete contact (i.e., bonding) of the element to the device may result in an incomplete mixing of a fluid sample. As a result, the element will typically have a fluid or gel layer (not shown) disposed between the element 702 and the external surface of the device 704, e.g., water. This fluid layer will generally be incorporated within a membrane, e.g., a latex balloon, having one surface in contact with the external surface of the reaction chamber and another surface in contact with the PZT element. An appropriately programmed computer 714 may be used to control the application of a voltage to the PZT element, via a function generator 712 and RF amplifier 710 to control the rate and/or timing of mmixing.

In alternate aspects, mixing may be supplied by the incorporation of ferromagnetic elements within the device which may be vibrated by supplying an alternating current to a coil adjacent the device. The oscillating current creates an oscillating magnetic field through the center of the coil which results in vibratory motion and rotation of the magnetic particles in the device, resulting in mixing, either by direct convection or accoustic streaming.

In addition to the above elements, the devices of the present invention may include additional components for optimizing sample preparation or analysis. For example, electrophoretic force may be used to draw target molecules into the surface of the array. For example, electrodes may be disposed or patterned on the surface of the array or on the surface opposite the array. Application of an appropriate electric field will either push or pull the targets in solution onto the array. A variety of similar enhancements can be included without departing from the scope of the invention.

Although it may often be desirable to incorporate all of the above described elements within a single disposable unit, generally, the cost of some of these elements and materials from which they are fabricated, can make it desirable to provide a unit that is at least partially reusable. Accordingly, in a particularly preferred embodiment, a variety of control elements for the device, e.g., temperature control, mixing and fluid transport elements may be supplied within a reusable base-unit.

For example, in a particularly preferred embodiment, the reaction chamber portion of the device can be mated with a reusable base unit that is adapted for receiving the device. As described, the base unit may include one or more heaters for controlling the temperature within selected reaction chambers within the device. Similarly, the base unit may incorporate mixing elements such as those described herein, as well as vacuum or pressure sources for providing sample mixing and transportation within the device.

As an example, the base unit may include a first surface having disposed thereon, one or more resistive heaters of the type described above. The heaters are positioned on the surface of the base unit such that when the reaction chamber device is mated to that surface, the heaters will be adjacent to and preferably contacting the exterior surface of the device adjacent to one or more reaction chambers in which temperature control is desired. Similarly, one or more mixing elements, such as the acoustic mixing elements described above, may also be disposed upon this surface of the base unit, whereby when mated with the reaction chamber device, the mixing elements contact the outer surface of the reaction/storage/analytical chambers in which such mixing is desired. For those reaction chambers in which both mixing and heating are desired, interspersed heaters and mixers may be provided on the surface of the base unit.

Alternatively, the base unit may include a second surface which contacts the opposite surface of the device from the first surface, to apply heating on one exterior surface of the reaction chamber and mixing at the other.

Along with the various above-described elements, the base unit also typically includes appropriate electrical connections for linking the heating and mixing elements to an appropriate power source. Similarly, the base unit may also be used to connect the reaction chamber device itself to external power sources, pressure/vacuum sources and the like. In particular, the base unit can provide manifolds, ports and electrical connections which plug into receiving connectors or ports on the device to provide power, vacuum or pressure for the various control elements that are internal to the device. For example, mating of the device to the base unit may provide a connection from a vacuum source in the base unit to a main vacuum manifold manufactured into the device, as described above. Similarly, the base unit may provide electrical connectors which couple to complementary connectors on the device to provide electrical current to any number of operations within the device via electrical circuitry fabricated into the device. Similarly, appropriate connections are also provided for monitoring various operations of the device, e.g., temperature, pressure and the like.

For those embodiments employing a pneumatic manifold for fluid transport which relies on the piercing of rupture membranes within the device to move the sample to subsequent chambers, the base unit will also typically include one or more solenoid mounted rupture pins. The solenoid mounted rupture pins are disposed within receptacles which are manufactured into the surface of the base unit, which receptacles correspond to positions of the rupture membranes upon the device. The pins are retained below the surface of the base unit when not in operation. Activation of the solenoid extends the pin above the surface of the base unit, into and through the rupture membrane.

Figure 8:
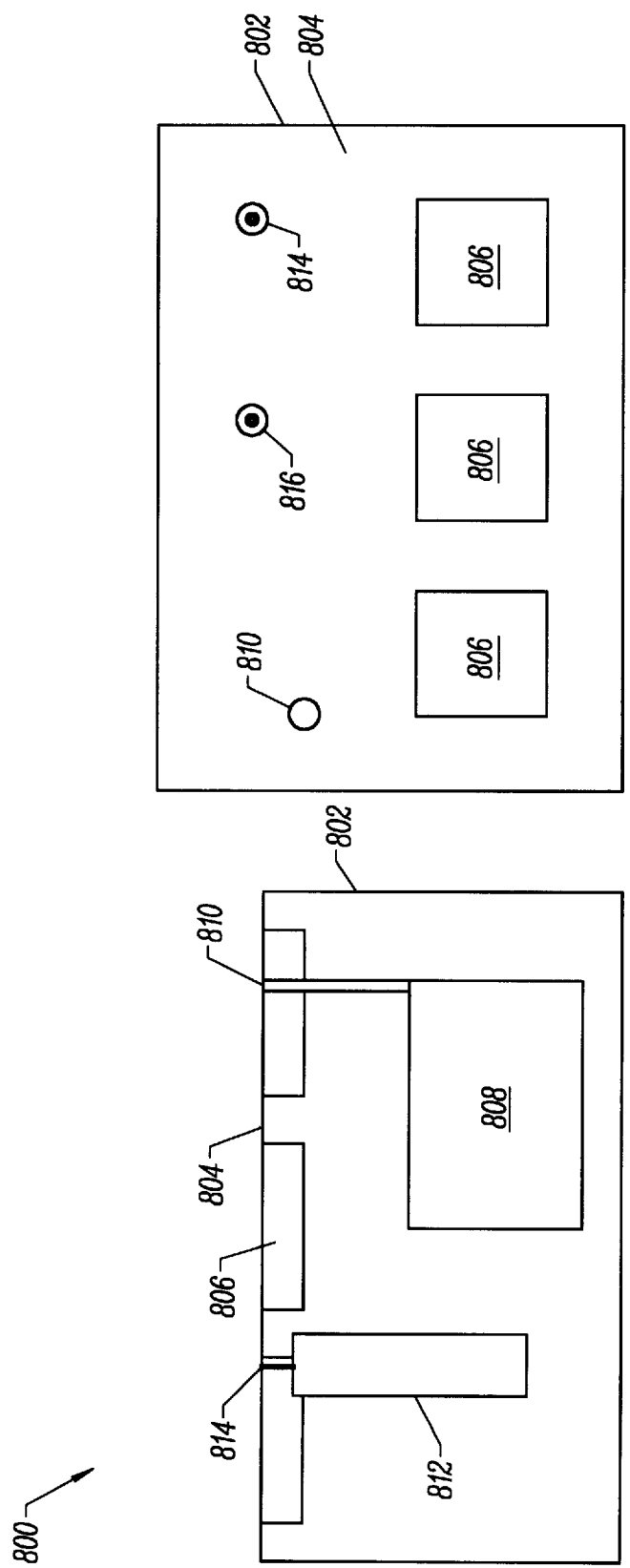
FIG. 8 is a schematic illustration of a side and top view of a base-unit for use with a miniature integrated device.

A schematic representation of one embodiment of a base unit is shown in FIG. 8. As shown in FIG. 8, the base unit 800 includes a body structure 802 having a mating surface 804. The body structure houses the various elements that are to be incorporated into the base unit. The base unit may also include one or more thermoelectric heating/cooling elements 806 disposed within the base unit such that when the reaction chamber contianing portion of the apparatus is mated to the mating surface of the base unit, the reaction chambers will be in contact or immediatly adjacent to the heating elements. For those embodiments employing a differential pressure based system for moving fluids within the device, as described above, the base unit may typically include a pressure source opening to the mating surface via the pressure source port 810. The base unit will also typically include other elements of these systems, such as solenoid 812 driven pins 814 for piercing rupture membranes. These pins are typically within recessed ports 816 in the mating surface 804. The base unit will also typically include mounting structures on the mating surface to ensure proper mating of the reaction chamber containing portion of the device to the base unit. Such mounting structures generally include mounting pins or holes (not shown) disposed on the mating surface which correspond to complementary structures on the reaction chamber containing portion of the device. Mounting pins may be differentially sized, and/or tapered, to ensure mating of the reaction chamber and base unit in an appropriate orientation. Alternatively, the base unit may be fabricated to include a well in which the reaction chamber portion mounts, which well has a nonsymetrical shape, matching a nonsymetrical shape of the reaction chamber portion. Such a design is similar to that used in the manufacture of audio tape cassettes and players.

In addition to the above described components, the device of the present invention may include a number of other components to further facilitate analyses. In particular, a number of the operations of sample transport, manipulation and monitoring may be performed by elements external to the device, per se. These elements may be incorporated within the above-described base unit, or may be included as further attachments to the device and/or base unit. For example, external pumps or fluid flow devices may be used to move the sample through the various operations of the device and/or for mixing, temperature controls may be applied externally to the device to maximize individual operations, and valve controls may be operated externally to direct and regulate the flow of the sample. In preferred embodiments, however, these various operations will be integrated within the device. Thus, in addition to the above described components, the integrated device of the invention will typically incorporate a number of additional components for sample transporting, direction, manipulation, and the like. Generally, this will include a plurality of micropumps, valves, mixers and heating elements.

Pumping devices that are particularly useful include a variety of micromachined pumps that have been reported in the art. For example, suitable pumps include pumps which having a bulging diaphragm, powered by a piezoelectric stack and two check valves, such as those described in U.S. Pat. Nos. 5,277,556, 5,271,724 and 5,171,132, or powered by a thermopneumatic element, as described in U.S. Pat. No. 5,126,022 piezoelectric peristaltic pumps using multiple membranes in series, and the like. The disclosure of each of these patents is incorporated herein by reference. Published PCT Application No. WO 94/05414 also discusses the use of a lamb-wave pump for transportation of fluid in micron scale channels.

Ferrofluidic fluid transport and mixing systems may also be incorporated into the device of the present invention. Typically, these systems incorporate a ferrofluidic substance which is placed into the apparatus. The ferrofluidic substance is controlled/directed externally through the use of magnets. In particular, the ferrofluidic substance provides a barrier which can be selectively moved to force the sample fluid through the apparatus, or through an individual operation of the apparatus. These ferrofluidic systems may be used for example, to reduce effective volumes where the sample occupies insufficient volume to fill the hybridization chamber. Insufficient sample fluid volume may result in incomplete hybridization with the array, and incomplete hybridization data. The ferrofluidic system is used to sandwich the sample fluid in a sufficiently small volume. This small volume is then drawn across the array in a manner which ensures the sample contacts the entire surface of the array. Ferrofluids are generally commercially available from, e.g., FerroFluidics Inc., New Hampshire.

Alternative fluid transport mechanisms for inclusion within the device of the present invention include, e.g. electrohydrodynamic pumps (see, e.g., Richter, et al. 3rd IEEE Workshop on Micro Electro Mechanical Systems, Feb. 12–14, 1990, Napa Valley, USA, and Richter et al., Sensors and Actuators 29:159–165 (1991), U.S. Pat. No. 5,126,022, each of which is incorporated herein by reference in its entirety for all purposes). Typically, such pumps employ a series of electrodes disposed across one surface of a channel or reaction/pumping chamber. Application of an electric field across the electrodes results in electrophoretic movement of nucleic acids in the sample. Indium-tin oxide films may be particularly suited for patterning electrodes on crystalline surfaces, e.g., a glass or silicon substrate. These methods can also be used to draw nucleic acids onto an array. For example, electrodes may paterned on the surface of an array substrate and modified with suitable functional groups for coupling nucleic acids to the surface of the electrodes. Application of a current betwen the electrodes on the surface of an array and an opposing electrode results in electrophoretic movement of the nucleic acids toward the surface of the array.

Electrophoretic pumping by application of transient electric fields can also be employed to avoid electrolysis at the surface of the electrodes while still causing sufficient sample movement. In particular, the electrophoretic mobility of a nucleic acid is not constant with the electric field applied. An increase in an electric field of from 50 to 400 v/cm results in a 30% increase in mobility of a nucleic acid sample in an acrylamide gel. By applying an oscillating voltage between a pair of electrodes capacitively coupled to the electrolyte, a net electrophoretic motion can be obtained without a net passage of charge. For example, a high electric field is applied in the forward direction of sample movement and a lower field is then applied in the reverse direction. See, e.g., Luckey, et al., Electrophoresis 14:492–501 (1993).

The above described micropumps may also be used to mix reagents and samples within the apparatus, by directing a recirculating fluid flow through the particular chamber to be mixed. Additional mixing methods may also be employed. For example, electrohydrodynamic mixers may be employed within the various reaction chambers. These mixers typically employ a traveling electric field for moving a fluid into which a charge has been introduced. See Bart, et al., Sensors and Actuators (1990) A21–A-23:193–197. These mixing elements can be readily incorporated into miniaturized devices. Alternatively, mixing may be carried out using thermopneumatic pumping mechanism. This typically involves the inclusion of small heaters, disposed behind apertures within a particular chamber. When the liquid in contact with the heater is heated, it expands through the apertures causing a convective force to be introduced into the chamber, thereby mixing the sample. Alternatively, a pumping mechanism retained behind two one way check valves, such as the pump described in U.S. Pat. No. 5,375,979 to Trah, incorporated herein by reference in its entirety for all purposes, can be employed to circulate a fluid sample within a chamber. In particular, the fluid is drawn into the pumping chamber through a first one-way check valve when the pump is operated in its vacuum or drawing cycle. The fluid is then expelled from the pump chamber through another one way check valve during the reciprocal pump cycle, resulting in a circular fluid flow within the reaction chamber. The pumping mechanism may employ any number of designs, as described herein, i.e., diaphragm, thermal pressure, electrohydrodynamic, etc.

It will typically be desirable to insulate electrical components of the device which may contact fluid samples, to prevent electrolysis of the sample at the surface of the component. Generally, any number of non-conducting insulating materials may be used for this function, including, e.g., teflon coating, $SiO_2$, $Si_3N_4$, and the like. Preferably, insulating layers will be $SiO_2$, which may generally be sputtered over the surface of the component to provide an insulating layer.

The device of the present invention will also typically incorporate a number of microvalves for the direction of fluid flow within the device. A variety of microvalve designs are particularly well suited for the instant device. Examples of valves that may be used in the device are described in, e.g., U.S. Pat. No. 5,277,556 to van Lintel, incorporated herein by reference. Preferred valve structures for use in the present devices typically incorporate a membrane or diaphragm which may be deflected onto a valve seat. For example, the electrostatic valves, silicon/aluminum bimetallic actuated valves or thermopneumatic actuated valves can be readily adapted for incorporation into the device of the invention. Typically, these valves will be incorporated within or at one or both of the termini of the fluid channels linking the various reaction chambers, and will be able to withstand the pressures or reagents used in the various operations. An illustration of an embodiment of the diaphragm valve/fluid channel construction is illustrated in FIG. 3.

The device may also incorporate one or more filters for removing cell debris and protein solids from the sample. The filters may generally be within the apparatus, e.g., within the fluid passages leading from the sample preparation/extraction chamber. A variety of well known filter media may be incorporated into the device, including, e.g., cellulose, nitrocellulose, polysulfone, nylon, vinyl/acrylic copolymers, glass fiber, polyvinylchloride, and the like. Alternatively, the filter may be a structure fabricated into the device similar to that described in U.S. Pat. No. 5,304,487 to Wilding et al., previously incorporated herein. Similarly, separation chambers having a separation media, e.g., ion exchange resin, affinity resin or the like, may be included within the device to eliminate contaminating proteins, etc.

In addition to sensors for monitoring temperature, the device of the present invention may also contain one or more sensors within the device itself to monitor the progress of one or more of the operations of the device. For example, optical sensors and pressure sensors may be incorporated to monitor the progress of the various reactions.

As described previously, reagents used in each operation integrated within the device may be exogenously introduced into the device, e.g., through sealable openings in each respective chamber. However, in preferred aspects, these reagents will be predisposed within the device. For example, these reagents may be disposed within the reaction chamber which performs the operation for which the reagent will be used, or within the fluid channels leading to that reaction chamber. Alternatively, the reagents may be disposed within storage chambers adjacent to and fluidly connected to their respective reaction chambers, whereby the reagents can be readily transported to the appropriate chamber as needed. For example, the amplification chamber will typically have the appropriate reagents for carrying out the amplification reaction, e.g., primer probe sequences, deoxynucleoside triphosphates ("dNTPs"), nucleic acid polymerases, buffering agents and the like, predisposed within the amplification chamber. Similarly, sample stabilization reagents will typically be predisposed within the sample collection chamber.

IV. Applications

The device and system of the present invention has a wide variety of uses in the manipulation, identification and/or sequencing of nucleic acid samples. These samples may be derived from plant, animal, viral or bacterial sources. For example, the device and system of the invention may be used in diagnostic applications, such as in diagnosing genetic disorders, as well as diagnosing the presence of infectious agents, e.g., bacterial or viral infections. Additionally, the device and system may be used in a variety of characterization applications, such as forensic analysis, e.g., genetic fingerprinting, bacterial, plant or viral identification or characterization, e.g., epidemiological or taxonomic analysis, and the like.

Although generally described in terms of individual devices, it will be appreciated that multiple devices may be provided in parallel to perform analyses on a large number of individual samples because the devices are miniaturized, reagent and/or space requirements are substantially reduced. Similarly, the small size allows automation of sample introduction process using, e.g., robot samplers and the like.

In preferred aspects, the device and system of the present invention is used in the analysis of human samples. More particularly, the device is used to determine the presence or absence of a particular nucleic acid sequence within a particular human sample. This includes the identification of genetic anomalies associated with a particular disorder, as well as the identification within a sample of a particular infectious agent, e.g., virus, bacteria, yeast or fungus.

The devices of the present invention may also be used in de novo sequencing applications. In particular, the device may be used in sequencing by hybridization (SBH) techniques. The use of oligonucleotide arrays in de novo SBH applications is described, for example, in U.S. application Ser. No. 08/082,937, filed Jun. 25, 1993, now abandoned.

EXAMPLES

Example 1—Acoustic Mixing

The efficacy of an acoustic element for mixing the contents of a reaction chamber was tested. A 0.5"×0.5"×0.04" crystal of PZT-5H was bonded to the external surface of a 0.030" thick region of a planar piece of delrin which had cavity machined in the surface opposite the PZT element. An oligonucleotide array synthesized on a flat silica substrate, was sealed over the cavity using a rubber gasket, such that the surface of the array having the oligonucleotide probes synthesized on it was exposed to the cavity, yielding a 250 µl reaction chamber. The PZT crystal was driven by an ENI200 High Frequency Power Supply, which is driven by a function generator from Hewlett Packard that was gated by a second function generator operated at 1 Hz.

Figure 7B:
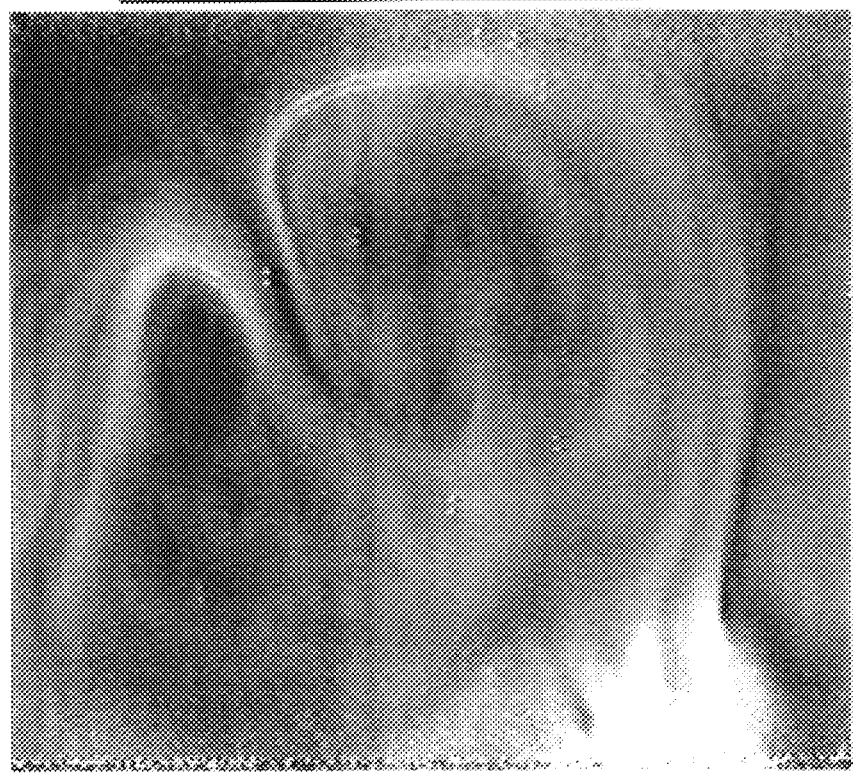
FIG. 7B shows mixing within a reaction chamber applying the PZT mixing element as shown in FIG. 7A.
Figure 7B:
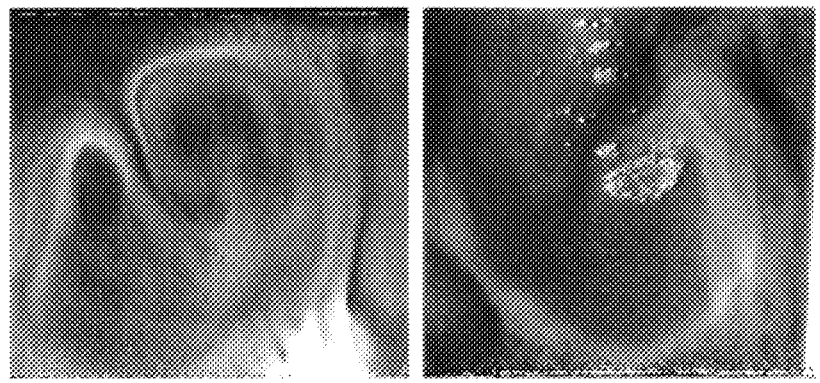
Figure 7B:
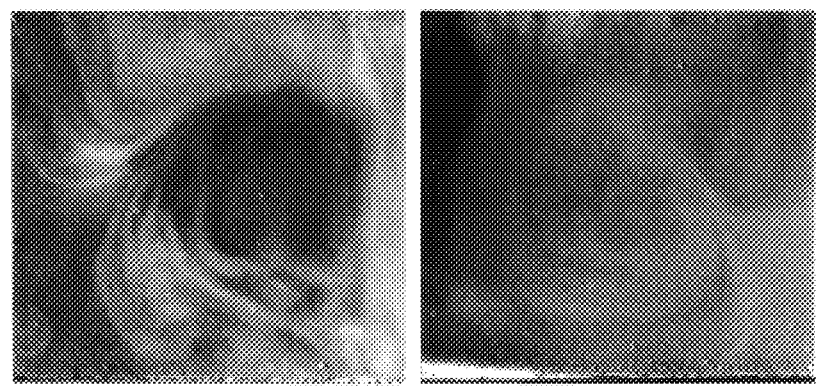
Figure 7C:
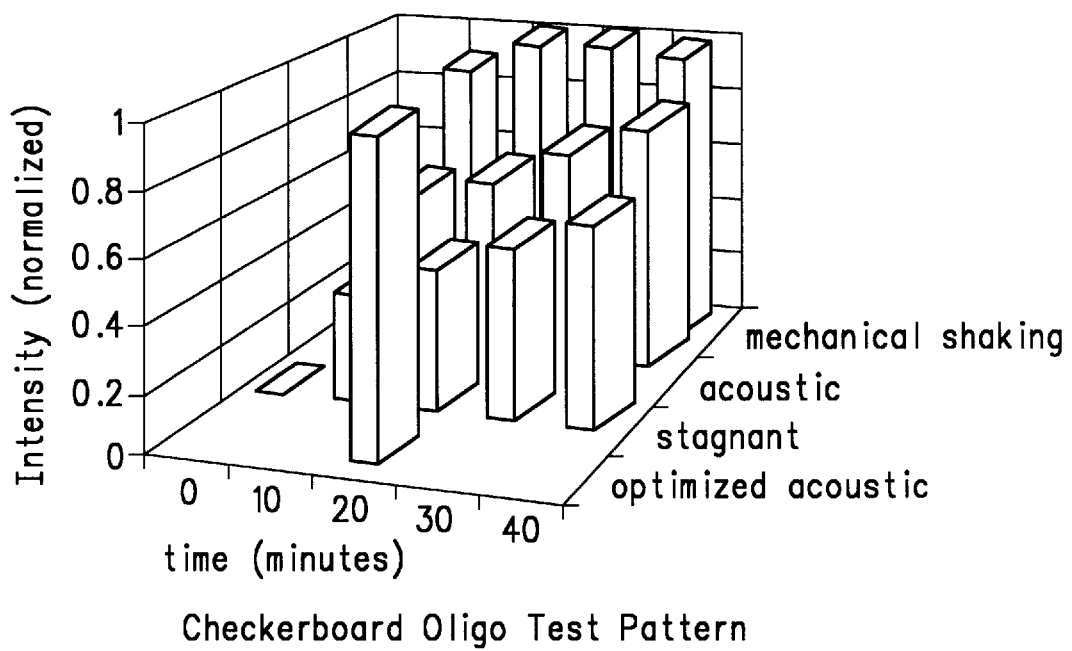
FIG. 7C is a bar graph showing a comparison of hybridization intensities using mechanical mixing, acoustic mixing, stagnant hybridization and optimized acoustic mixing.

In an initial test, the chamber was filled with deionized water and a small amount of 2% milk was injected for visualization. The crystal was driven at 2 MHz with an average power of 3 W. Fluid velocities within the chamber were estimated in excess of 1 mm/sec, indicating significant convection. A photograph showing this convection is shown in FIG. 7B.

The efficacy of acoustic mixing was also tested in an actual hybridization protocol. For this hybridization test, a fluorescently labeled oligonucleotide target sequence having the sequence 5'-GAGATGCGTCGGTGGCTG-3' and an array having a checkerboard pattern of 400 µm squares having complements to this sequence synthesized thereon, were used. Hybridization of a 10 nM solution of the target in 6xSSPE was carried out. During hybridization, the external surface of the array was kept in contact with a thermoelectric cooler set at 15° C. Hybridization was carried out for 20 minutes while driving the crystal at 2 MHz at an average power of 4 W (on time=0.2 sec., off time=0.8 sec.). The resulting average intensity was identical to that achieved using mechanical mixing of the chamber (vertical rotation with an incorporated bubble).

Additional experiments using fluorescently labeled and fragmented 1 kb portion of the HIV virus had a successful base calling rates. In particular, a 1 kb HIV nucleic acid segment was sequenced using an HIV tiled oligonucleotide array or chip. See, U.S. patent application Ser. No. 08/284,064, filed Aug. 2, 1994, and incorporated herein by reference for all purposes. Acoustic mixing achieved a 90.5% correct base calling rate as compared to a 95.8% correct base calling rate for mechanical mixing.

Example 2—RNA Preparation Reactions in Miniaturized System

A model miniature reactor system was designed to investigate the efficacy of miniaturized devices in carrying out prehybridization preparative reactions on target nucleic acids. In particular, a dual reaction chamber system for carrying out in vitro transcription and fragmentation was fabricated. The device employed a tube based structure using a polymer tubing as an in vitro transcription reactor coupled to a glass capillary fragmentation reactor. Reagents not introduced with the sample were provided as dried deposits on the internal surface of the connecting tubing. The experiment was designed to investigate the effects of reaction chamber materials and reaction volume in RNA preparative reaction chambers.

Figure 10A:
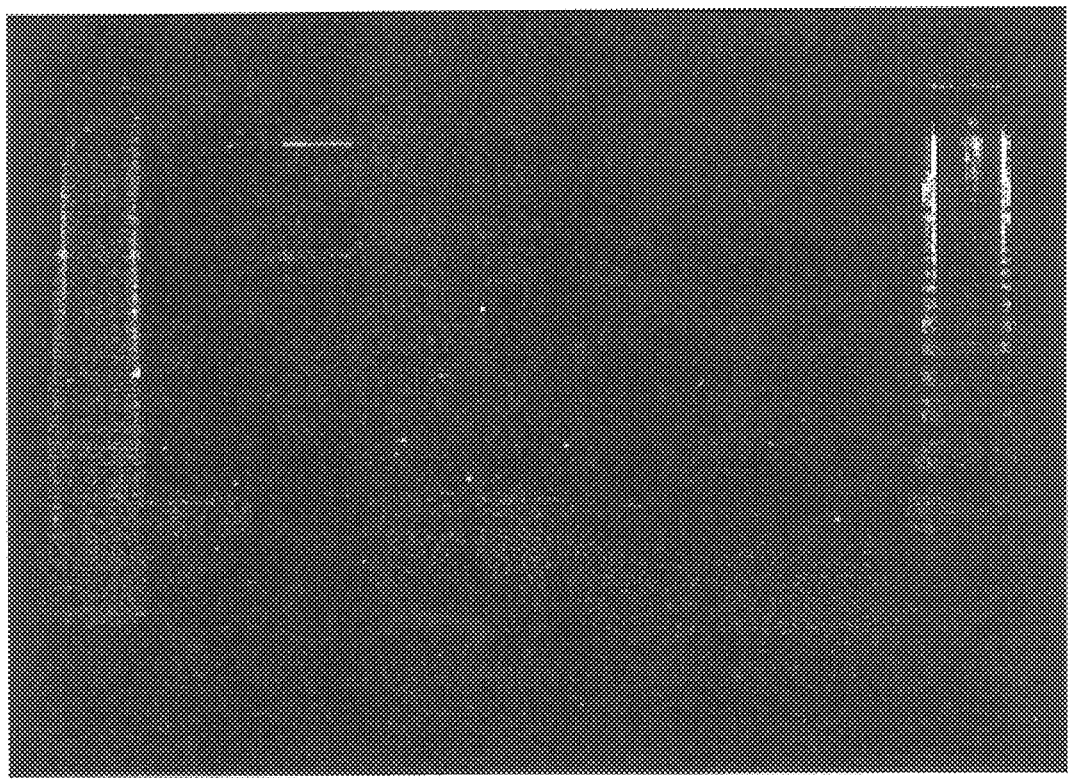
FIG. 10A is a gel showing a time course of an RNA fragmentation reaction in a microchamber.

The sample including the target nucleic acid, DNA amplicons containing a 1 kb portion of the HIV gene flanked with promoter regions for the T3 and T7 RNA primers on the sense and antisense strands, respectively, RNA polymerase, NTPs, fluorinated UTP and buffer, were introduced into the reactor system at one end of the tubing based system. In vitro transcription was carried out in a silicone tubing reactor immersed in a water bath. Following this initial reaction, the sample was moved through the system into a glass capillary reactor which was maintained at 94° C., for carrying out the fragmentation reaction. The products of this fragmentation reaction are shown in the gel of FIG. 10A. In some cases, the tubing connecting the IVT reactor to the fragmentation reactor contained additional $MgCl_2$ for addition to the sample. The glass capillary was first coated with BSA to avoid interactions between the sample and the glass. Following fragmentation, the sample was hybridized with an appropriately tiled oligonucleotide array, as described above. Preparation using this system with 14 mM $MgCl_2$ addition resulted in a correct base calling rate of 96.5%. Omission of the $MgCl_2$ gave a correct base calling rate of 95.5%.

A similar preparative transcription reaction was carried out in a micro-reaction chamber fabricated in polycarbonate. A well was machined in the surface of a first polycarbonate part. The well was 250 µm deep and had an approximate volume of 5 µl. A second polycarbonate part was then acoustically welded to the first to provide a top wall for the reaction chamber. The second part had two holes drilled through it, which holes were positioned at opposite ends of the reaction chamber. Temperature control for the transcription reaction was supplied by applying external temperature controls to the reaction chamber, as described for the tubing based system. 3 µl samples were used for both transcription and fragmentation experiments.

Figure 10B:
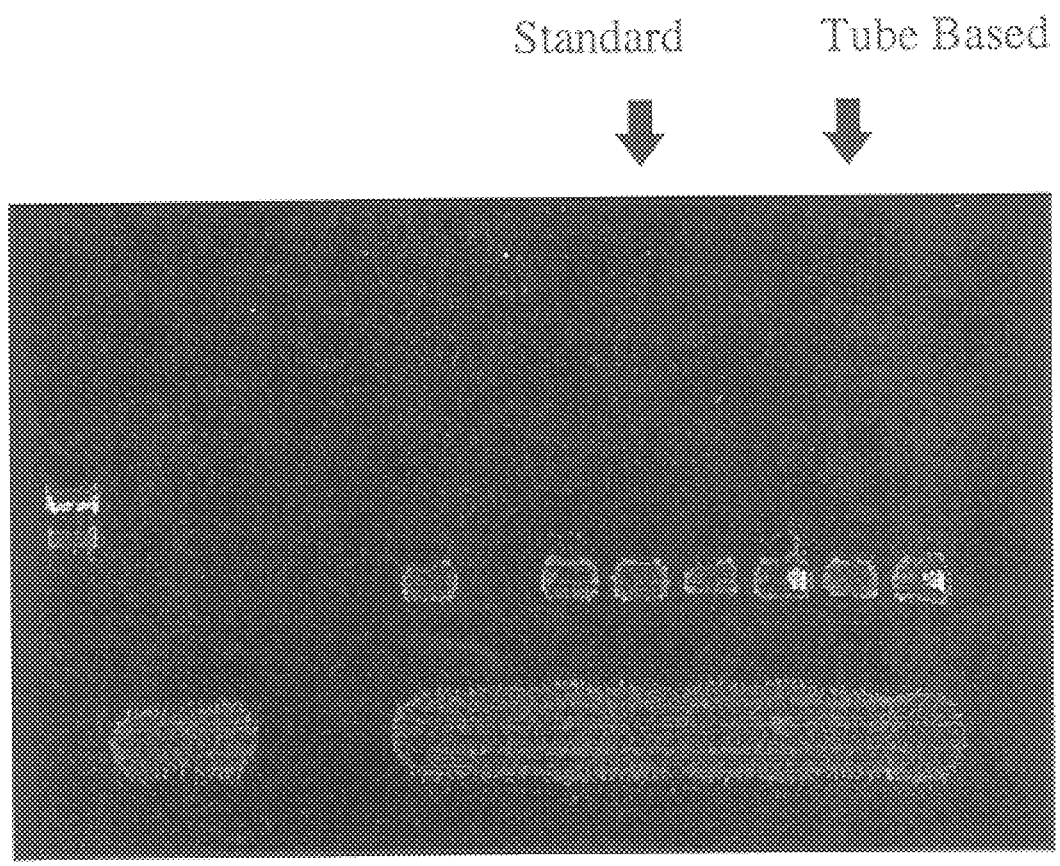
FIG. 10B is a gel showing a comparison of the product of an in vitro transcription reaction in a microchamber vs. a control (test tube).

Transcription reactions performed in the micro-reactor achieved a 70% yield as compared to conventional methods, e.g., same volume in microfuge tube and water bath or PCR thermal cycler. A comparison of in vitro transcription reaction products using a microchamber versus a larger scale control are shown in FIG. 10B.

Example 3—PCR Amplification in Miniaturized System

The miniature polymeric reaction chamber similar to the one described in Example 2 was used for carrying out PCR amplification. In particular, the chamber was fabricated from a planar piece of poycarbonate 4 mm thick, and having a cavity measuring 500 μm deep machined into its surface. A second planar polycarbonate piece was welded over the cavity. This second piece was only 250 μm thick. Thermal control was supplied by applying a peltier heater against the thinner second wall of the cavity.

Figure 9:
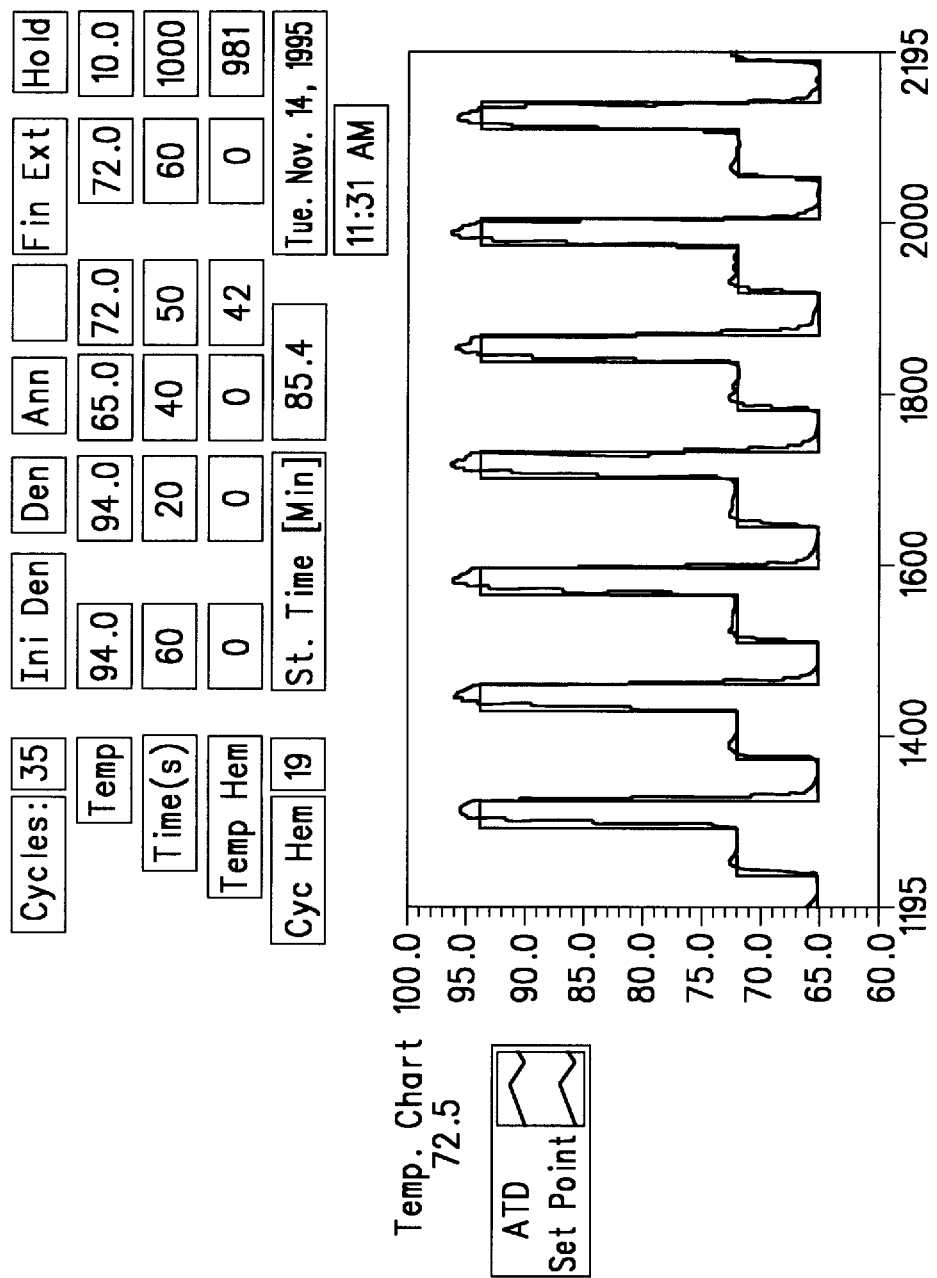
FIG. 9 is a time temperature profile of thermal cycling in a miniature reaction chamber and a display of the programmed cycling parameters.
Figure 10C:
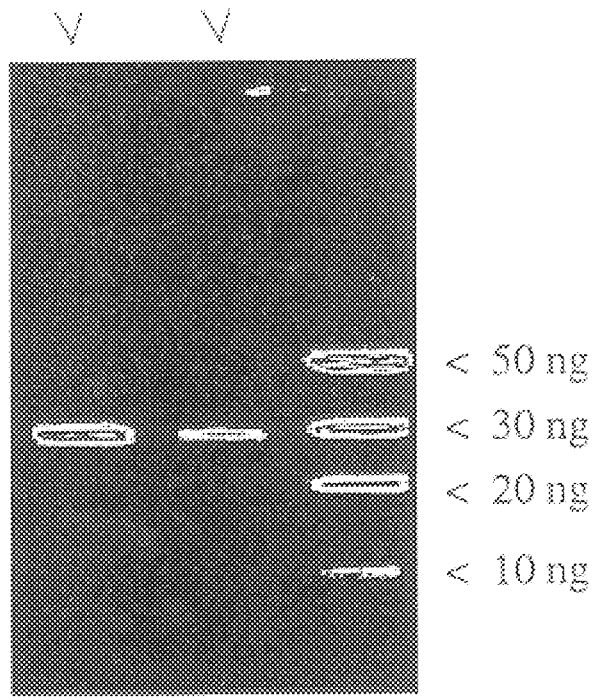
FIG. 10C is a comparison of the PCR product produced in a PCR thermal cycler and that produced by a microreactor.

Amplification of a target nucleic acid was performed with Perkin-Elmer GeneAmp® PCR kit. The reaction chamber was cycled for 20 seconds at 94° C. (denaturing), 40 seconds at 65° C. (annealing) and 50 seconds at 72° C. (extension). A profile of the thermal cycling is shown in FIG. 9. Amplification of approximately $10^9$ was shown after 35 cycles. FIG. 10C shows production of amplified product in the microchamber as compared to a control using a typical PCR thermal cycler.

While the foregoing invention has been described in some detail for purposes of clarity and understanding, it will be clear to one skilled in the art from a reading of this disclosure that various changes in form and detail can be made without departing from the true scope of the invention. In addition, the present invention is further described by reference to the attached appendix. All publications and patent documents cited in this application are incorporated by reference in their entirety for all purposes to the same extent as if each individual publication or patent document were so individually denoted.

What is claimed is:

1. A miniature analytical device, comprising:
   a body having at least a first reaction chamber fluidly connected to a second reaction chamber by a fluid passage;
   a sample inlet, fluidly connected to said first reaction chamber, for introducing a fluid sample into said device;
   a differential pressure delivery system for maintaining said first reaction chamber at a first pressure and said second reaction chamber at a second pressure, said first pressure being greater than ambient pressure and said second pressure being greater than said first pressure, whereby when said second reaction chamber is brought to ambient pressure, said first pressure forces a liquid sample in said first reaction chamber into said second reaction chamber;
   a pressure source;
   at least first and second passages fluidly connecting said pressure source to said first and second reaction chambers, respectively;
   a first fluidic resistance disposed in said first passage between said pressure source and said first reaction chamber, said first fluidic resistance transforming a pressure from said pressure source to said first pressure;
   a second fluidic resistance disposed in said second passage between said pressure source and said second reaction chamber, said second fluidic resistance transforming said pressure from said pressure source to said second pressure; and
   first and second openable closures in said first and second reaction chambers, respectively, whereby opening of said first or second closures allows said first or second reaction chambers to achieve ambient pressure.

2. The miniature device of claim 1, wherein said first and second fluidic resistances independently comprise one or more fluid passages connecting said first and second passages to said first and second reaction chambers, said first fluidic resistance having a smaller cross-sectional area than said second fluidic resistance.

3. A miniature analytical device, comprising:
   a body having at least a first reaction chamber fluidly connected to a second reaction chamber by a fluid passage;
   a sample inlet, fluidly connected to said first reaction chamber, for introducing a fluid sample into said device;
   a differential pressure delivery source for maintaining said first reaction chamber at a first pressure and said second reaction chamber at a second pressure, said second pressure being less than ambient pressure and said first pressure being less than said second pressure, whereby when said first reaction chamber is brought to ambient pressure, said second pressure draws a liquid sample in said first reaction chamber into said second reaction chamber, said differential pressure delivery system comprising a pressure source;
   at least first and second passages fluidly connecting said pressure source to said first and second reaction chambers, respectively;
   a first fluidic resistance disposed in said first passage between said pressure source and said first reaction chamber, said first fluidic resistance transforming a pressure from said pressure source to said first pressure;
   a second fluidic resistance disposed in said second passage between said pressure source and said second reaction chamber, said second fluidic resistance transforming said pressure from said pressure source to said second pressure; and
   first and second openable closures in said first and second reaction chambers, respectively, whereby opening of said first or second closures allows said first or second reaction chambers to achieve ambient pressure.

4. The miniature device of claim 3, wherein said first and second fluidic resistances independently comprise one or more fluid passages connecting said first and second passages to said first and second reaction chambers, said first fluidic resistance having a larger cross sectional area than said second fluidic resistance.

* * * * *